United States Patent
Botvinick et al.

(10) Patent No.: US 9,357,952 B2
(45) Date of Patent: *Jun. 7, 2016

(54) IMPLANTABLE BIOSENSOR AND METHODS OF USE THEREOF

(71) Applicant: Metronom Health, Inc., Laguna Hills, CA (US)

(72) Inventors: Elliot Botvinick, Irvine, CA (US); Troy M. Bremer, Irvine, CA (US)

(73) Assignee: Metronom Health, Inc., Laguna Hills, CA (US)

( * ) Notice: Subject to any disclaimer, the term of this patent is extended or adjusted under 35 U.S.C. 154(b) by 164 days.

This patent is subject to a terminal disclaimer.

(21) Appl. No.: 14/034,218

(22) Filed: Sep. 23, 2013

(65) Prior Publication Data

US 2014/0163345 A1 Jun. 12, 2014

Related U.S. Application Data

(60) Continuation of application No. 11/427,641, filed on Jun. 29, 2006, now Pat. No. 8,543,182, which is a division of application No. 11/013,997, filed on Dec. 16, 2004, now Pat. No. 7,146,203.

(60) Provisional application No. 60/531,447, filed on Dec. 18, 2003.

(51) Int. Cl.
| | | |
|---|---|---|
| A61B 5/00 | (2006.01) | |
| G01F 1/64 | (2006.01) | |
| C12Q 1/00 | (2006.01) | |
| C12Q 1/54 | (2006.01) | |
| A61B 5/145 | (2006.01) | |
| A61B 5/1486 | (2006.01) | |
| A61B 5/1459 | (2006.01) | |
| A61B 5/1473 | (2006.01) | |

(52) U.S. Cl.
CPC ........... *A61B 5/14532* (2013.01); *A61B 5/1459* (2013.01); *A61B 5/1473* (2013.01); *A61B 5/14865* (2013.01)

(58) Field of Classification Search
USPC .......... 600/345–347, 357, 360, 365; 205/778, 205/782.5, 792; 435/4, 14
See application file for complete search history.

(56) References Cited

U.S. PATENT DOCUMENTS

| | | |
|---|---|---|
| 4,336,248 A | 6/1982 | Bonhard et al. |
| 4,986,271 A | 1/1991 | Wilkins et al. |
| 5,091,991 A | 2/1992 | Briggs et al. |
| 5,391,250 A | 2/1995 | Cheney, II et al. |
| 5,443,080 A | 8/1995 | D'Angelo et al. |
| 5,733,563 A | 3/1998 | Fortier |
| 5,756,209 A | 5/1998 | Hale |
| 6,074,607 A | 6/2000 | Slovacek et al. |
| 6,172,261 B1 | 1/2001 | Vermeulin et al. |
| 6,249,638 B1 | 6/2001 | Hale |
| 6,325,978 B1 | 12/2001 | Labuda et al. |
| 6,340,588 B1 | 1/2002 | Nova et al. |
| 6,387,379 B1 | 5/2002 | Goldberg et al. |
| 6,679,841 B2 | 1/2004 | Bojan et al. |
| 6,771,860 B2 | 8/2004 | Trezza et al. |
| 6,773,703 B1 | 8/2004 | Ettner |
| 6,960,031 B2 | 11/2005 | McFarland et al. |
| 7,054,514 B2 | 5/2006 | Uchiyama et al. |
| 7,160,923 B1 | 1/2007 | Vermeulin et al. |
| 7,405,055 B2 | 7/2008 | Dunn et al. |
| 7,413,781 B2 | 8/2008 | Hubbell et al. |
| 7,625,862 B2 | 12/2009 | Winslow et al. |
| 7,721,412 B2 | 5/2010 | Say et al. |
| 7,725,149 B2 | 5/2010 | Peyser et al. |
| 7,813,780 B2 | 10/2010 | Shah et al. |
| 7,860,354 B2 | 12/2010 | Uematsu et al. |
| 7,873,399 B2 | 1/2011 | Berner et al. |
| 7,935,499 B2 | 5/2011 | Dunn et al. |
| 7,989,414 B2 | 8/2011 | Winslow et al. |
| 8,377,868 B2 | 2/2013 | Winslow et al. |
| 8,543,182 B2 | 9/2013 | Botvinick et al. |
| 9,034,893 B2 | 5/2015 | Shafer et al. |
| 9,060,742 B2 | 6/2015 | Brister et al. |

*Primary Examiner* — Marsha Tsay
(74) *Attorney, Agent, or Firm* — Knobbe Martens Olson and Bear LLP

(57) ABSTRACT

Provided herein is a stabilized oxygen transport matrix that includes a reversible oxygen binding protein, such as hemoglobin, immobilized throughout the stabilized oxygen transport matrix. The stabilized oxygen transport matrix is used to transport oxygen and can be used as an oxygen transport region and a reaction region of an analyte sensor, such as an implantable glucose sensor. The reversible binding protein can also function as an oxygen probe within the analyte sensor.

15 Claims, 7 Drawing Sheets

IMPLANTABLE BIOSENSOR AND METHODS OF USE THEREOF

RELATED APPLICATION DATA

This application claims the benefit of priority under 35 U.S.C. §119(e)(1) of U.S. Ser. No. 60/531,447, filed Dec. 18, 2003, the entire content of which is incorporated herein by reference.

BACKGROUND OF THE INVENTION

1. Field of the Invention

The invention relates generally to glucose monitoring and more specifically to implantable glucose sensors.

2. Background Information

Diabetes is a disease of insufficient blood glucose regulation. In non-diabetic people, the body's beta cells monitor glucose and deliver just the right amount of insulin on a minute-by-minute basis for tissues in the body to uptake the right amount of glucose, keeping blood glucose at healthy levels. In diabetics this healthy regulation system primarily fails due to the following two factors, either alone or in combination: 1) insufficient insulin production and secretion, 2) a lack of normal sensitivity to insulin by the tissues of the body.

The first major breakthrough in treating diabetes was the discovery of insulin. The backbone of today's treatments relies on this discovery, and the patient's self-initiative and compliance. Two types of diabetes mellitus are common. Type 1 diabetes accounts for 5-10% of all cases, and Type 2 diabetes accounts for 90-95% of the diabetic population. In Type 1 diabetes, the disease requires insulin injections to maintain life, in addition it requires healthy eating and exercise. Treating type 2 diabetes may require insulin, but the disease may be controllable with oral medication, weight loss, a careful diet and a regular exercise program.

There is still no magic pill to treat diabetes. Current drugs have the potential to eliminate complications altogether, if only the patient knew when and how much to take. A program of very frequent sampling is required to provide both the rate and extent of glycemic excursions. This set of glucose measurements is absolutely necessary information to calculate the timing and amount of corrective actions needed to effectively treat Diabetes and prevent complications. The importance of blood glucose monitoring has been underscored by the results of the Diabetes Control and Complications Trial, which showed that many of the long-term complications of diabetes could be prevented by close blood glucose regulation.

However, current blood glucose tests are painful, requiring finger sticking to obtain a blood sample. They are inconvenient due to disruption of daily life and difficult to perform in long-term diabetic patients due to calluses on the fingers and poor circulation. With present technology, the average diabetic patient tests his/her blood glucose levels less than twice a day versus the recommended 4-7 times per day. Further, even the recommended testing schedule is far from sufficient to allow blood glucose normalization.

Thus with present technology, the necessary monitoring is frequently unachieved chore. The required sampling schedule cannot realistically be expected of even the most committed patients during the day and is not feasible at night. Present blood glucose monitoring methods are not automatic, chronically requiring user initiative. This system cannot therefore be relied upon to detect spontaneous hypoglycemia or other glycemic excursions. Consequently, even the most diligent patients fail to avoid severe complications. As a result $85 billion was spent in 2002 on treating Diabetes complications, including loss of sight, loss of kidney function, loss of limbs, vascular disease, heart failure, stroke, coma, and severe constant pain.

New glucose monitoring methods are needed to address these shortcomings An automatic, painless, and convenient means of continuous glucose monitoring could provide the information needed for adequate control. This would greatly reduce the complications seen in these patients and the associated health care costs of their treatment.

In order to meet the needs of continuous glucose monitoring for diabetes, the monitoring process must satisfy the following:

Require no sample preparation (the measurements occur automatically)

Be highly selective and sensitive

Provide a rapid response to changes in glucose

Provide highly repeatable/reproducible measurements

Operate with stability and low drift

A number of different technologies have been applied to develop a glucose sensor to meet these needs. However, the most direct route to bring a successful device to the market is to develop a disposable sensor that operates in the subcutaneous tissue. This minimizes the risk of serious complications associated with a fully implanted device.

A very successful method that satisfied all of the above requirements for biosensing is enzyme based ampermetric electrode sensing. This method was intended to operate in a homogenous oxygen environment with high oxygen availability, such as a major blood vessel in the body. The employed method consumed oxygen, effectively maintaining a zero oxygen concentration at the electrode surface in order to measure oxygen. However, this approach is not directly applicable to the subcutaneous tissue.

As is often the case, the type of sensing method applied will impact the ability to achieve success in new sensing environments. Many sensing methods will perform well under in vitro or carefully controlled conditions, but will then fail to perform well in the body. Their failure has been attributed to inadequate selectivity, electrode poisoning, and insufficient glucose sensitivity.

High glucose selectivity is essential to provide an accurate measurement of glucose in the body. The selectivity of a measurement refers to the degree to which a particular analyte may be determined in a complex mixture without interference from other constituents in the mixture. In the body, there is a complex mixture that may be termed the tissue matrix in which glucose must be measured. The tissue matrix contains many constituents that are constantly changing and which may interfere with varying types of measurement approaches. The constant state of flux of the tissue matrix prevents a calibration from being established for selective measurement through a technique such as multiple regression to remove the impact of unmeasured interfering constituents of the matrix.

A full range of approaches from non-invasive to invasive are being developed in an attempt to bring a new kind of glucose sensor to market. However, while appealing, non-invasive optical measurements are generally not sufficiently selective for glucose without a detailed knowledge of the matrix being probed. The optical measurement is performed by focusing a beam of energy onto the body. The energy is modified by the tissue after transmission through the target area. A signature of the tissue content is produced by the energy exiting the tissue. The energy leaving is a function of chemical components encountered as well as thickness, color and structure of the tissue matrix through which the energy passes. In the body, the tissue matrix is constantly changing. Additionally, constant changes in the external environment, and their impact on the skin provide a non-stationary environment. This poses a severe challenge for purely optical measurements to be highly selective for glucose.

To achieve sufficient selectivity for glucose, the enzyme glucose oxidase may be employed in a semi-invasive approach. Clark and Lyons first used the strategy of combining the specificity of a biological system to achieve the necessary selectivity for glucose measurements in a tissue matrix. Glucose oxidase has a high specificity for glucose. This enzyme reduces glucose to gluconic acid and peroxide in the presence of oxygen and water.

By coupling glucose oxidase with a suitable transducer, glucose concentration may be measured by monitoring either the production of peroxide or the consumption of oxygen.

However, problems exist in the direct application of both of these approaches. Hydrogen peroxide probes often suffer from electrochemical interference by oxidizable species in a complex matrix such as encountered in the body. The electrode oxidizes these other electroactive constituents as well as hydrogen peroxide, which results in measurements with a net positive and variable error. The hydrogen peroxide if not eliminated may also have an undesirable reaction with the surrounding tissue as well as degrade the oxidase enzyme necessary for the operation of the sensor over the course of sensor operation. Additionally, unless oxygen is available in excess to the glucose being reduced by the reaction, variations in bulk oxygen will also change how much glucose is oxidized, resulting in erroneous measurements if the oxygen concentration influencing the reaction is not directly accounted for in a calibration, or prevented from impacting reaction dynamics. The problem of sensitivity to varying oxygen concentration is also present in approaches based on measuring oxygen consumption. Unfortunately, the subcutaneous tissue environment has been shown to have both a variable and heterogeneous oxygen concentration. These measurements must therefore address background oxygen variations to accurately determine the amount of oxygen being consumed, necessary for accurate glucose measurement.

Thus, to effectively utilize glucose oxidase a series of problems should be overcome. First, sufficient oxygen should be available for the reaction to proceed. Second, regardless of how glucose oxidase is coupled to a transducer, if oxygen is not available in excess, as will be the case in the subcutaneous tissue, then knowledge of oxygen concentration is needed to provide a completely selective measurement of glucose. Third, glucose oxidase should be coupled to a detector in a manner satisfying the requirements of biosensing stated above.

Much work has been done on coupling glucose oxidase to an electrode. However, problems of stability, drift, selectivity, and sensitivity must be overcome if using an electrode system. Extensive efforts have been devoted for stabilizing the electrode, minimizing the error of electroactive interference, and preventing "electrode poisoning"; however, an alternative approach is to avoid using an electrode as a transducer by selecting an optical measurement method. In the subcutaneous environment, oxygen is scarce, making an optical method that measures the result of the glucose oxidation reaction while not consuming oxygen even more desirable.

In coupling glucose oxidase with an optical transducer, an additional problem of selective sensing of oxygen is posed. Fortunately, optical means of selectively sensing oxygen are well established.

SUMMARY OF THE INVENTION

The present invention is based, at least in part, on the discovery of a stabilized oxygen transport matrix that includes a reversible oxygen binding protein, such as hemoglobin, immobilized throughout the stabilized oxygen transport matrix. The stabilized matrix collects oxygen, stabilizes oxygen dynamics, and rapidly transports oxygen within the matrix. For example, the stabilized matrix can transport oxygen from a region of relatively high oxygen surrounding one surface of the stabilized matrix, to a region of lower or no oxygen on a second surface. Furthermore, the stabilized matrix can transport oxygen to a site within the matrix or juxtaposed to the matrix, where a reaction occurs in which oxygen is consumed.

The stabilized oxygen matrix provides numerous functions including rapid transport of oxygen in an implantable sensor and rapid transport of oxygen to an artificial tissue. Accordingly, provided herein in one embodiment is a method for transporting oxygen from a first area having a relatively high oxygen concentration to a second area having a relatively low oxygen concentration, that includes contacting oxygen from the first area, to a first surface of a stabilized oxygen transport matrix that includes a reversible oxygen binding protein immobilized throughout the stabilized oxygen transport matrix, and transporting oxygen away from the first surface of the stabilized oxygen transport matrix to a second surface of the oxygen transport matrix, wherein the second surface of the oxygen transport matrix contacts the second area.

In illustrative embodiments, the present invention is based, at least in part, on the discovery that the stabilized oxygen transport matrix can be used to rapidly transport oxygen in a biosensor, especially an implantable glucose sensor, to overcome challenges of implantable sensors, such as spatial and temporal changes in oxygen concentration at the site of an implant. Additionally, the present invention is based, at least in part, on the discovery that a substantially non-oxygen consuming probe can be coupled with a selective mediator such as glucose oxidase with appropriately defined geometry and boundary conditions to develop a glucose sensor that will operate accurately under low oxygen tension such as typical in the subcutaneous tissues. The reversible oxygen-binding protein transporter can be used to increase the supply of oxygen to the glucose oxidase reaction site in a more homogenous manner, providing an environment for the reaction to proceed that is more suitable for making sensitive glucose measurements with a broad dynamic range. Furthermore, a reversible oxygen binding protein, or an additional oxygen-sensitive dye, can be used to optically measure changes in oxygen concentration that result from the glucose-oxidase catalyzed reaction of glucose that is being mediated by oxygen. By choosing this approach, the issues of selectivity are overcome when a reference oxygen measurement is taken at a region in the glucose sensor that is distant from a site where glucose enters the sensor, but having an oxygen concentration (at the reference region) that provides a measure of the oxygen concentration that would have been present at the site where glucose enters the sensor in the absence of glucose.

In one embodiment, the present invention provides an enzymatic-based sensor capable of selectively and sensitively monitoring glucose in the subcutaneous tissues under low oxygen tensions. The sensor includes an oxygen transport region comprising a first reversible oxygen binding protein, an oxygen permeable first surface in communication with an external environment, and an oxygen permeable second surface which is impermeable to the target analyte; a target analyte reaction region in communication with the oxygen transport region at the oxygen permeable second surface, wherein the target analyte reaction region comprises a target analyte oxidase enzyme, and a target analyte-permeable surface; and a sensing region comprising at least one detector probe in communication with the target analyte reaction region. Typically, a target analyte and oxygen impermeable surface is located in the sensor such that the sensing region is in between the target analyte and oxygen impermeable surface and the oxygen transport region.

The target analyte can be, for example, glucose, galactose, lactose, peroxide, cholesterol, amino acids, alcohol, or lactic acid. In certain illustrative examples, the target analyte is glucose and the sensor is a glucose sensor. For example, the glucose sensor can be an implantable glucose sensor such as a transcutaneous glucose sensor.

The first reversible oxygen binding protein can be an engineered hemeprotein or a heme derivative. In illustrative examples, the first reversible oxygen binding protein is myoglobin or hemoglobin.

The sensing region can further include an oxygen probe. For example, the oxygen probe can be a second reversible oxygen binding protein, such as an engineered hemeprotein or a heme derivative. In illustrative examples, the first and the second reversible oxygen binding protein is hemoglobin.

In certain exemplary sensors provided herein, at least one substantially non-oxygen consuming detector probe is used. The detector probe can further include a spectrometer. At least one detector probe, in certain examples, is capable of emitting and/or receiving light at an oxygen sensitive engineered hemeprotein, or heme derivative absorption wavelength. For example, one or more emitters can emit light toward one or more receivers, and the emitters and the receivers can both enter the sensor through a first end. The one or more emitters can be one or more fiber optic fibers that are formed into a loop such that light exiting from the emitter fiber optic fibers travels in a path that is substantially opposite to light from a light source that enters the emitter fiber optic fibers.

In another embodiment, provided herein is a method for measuring a concentration of an analyte, comprising transporting oxygen from an external environment through an oxygen transport region within a sensor to an analyte reaction region of the sensor using a first reversible oxygen binding protein; reacting a portion of the transported oxygen with the analyte enzymatically in the analyte reaction region to form a product; and measuring oxygen or a product of the reaction of oxygen and the analyte in a sensing region comprising the analyte reaction region or a sensing region in contact with the analyte reaction region, thereby measuring the concentration of the analyte.

In illustrative aspects, the analyte being measured is glucose, galactose, lactose, peroxide, cholesterol, amino acids, alcohol, or lactic acid. In a particularly illustrative embodiment, the analyte being measured is glucose. The measuring can be performed repeatedly, for example at least at a first time point and a second time point, thereby providing information regarding changes in analyte concentration over time. In certain examples, oxygen is transported from the external environment comprising subcutaneous tissue to the analyte reaction region using an engineered hemeprotein or a heme derivative as the first reversible oxygen binding protein. For example, oxygen is transported from the external environment to the analyte reaction region using hemoglobin as the first reversible oxygen binding protein.

Oxygen can be measured, for example, by measuring oxygen binding of an oxygen probe. Oxygen binding can be measured using a spectrometer measuring absorption of the oxygen binding protein such as a second reversible binding protein. The second reversible oxygen binding protein can be an engineered hemeprotein or a heme derivative, such as hemoglobin. In illustrative aspects, hemoglobin is both the first reversibly binding protein and the second reversible binding protein.

The measuring is typically performed using one or more detector probes, for example a population of substantially non-oxygen consuming detector probes, emitting light towards one or more non-oxygen consuming receivers at an oxygen sensitive engineered hemeprotein or heme derivative wavelength. In certain aspects, light travels through one or more emitter fiber optic fibers from a light source emitting in a first direction, and then travels in a second direction that is substantially opposite the first direction through at least a portion of the sensing region where it is received by one or more receiver fiber optic fibers. In a related aspect, light travels through one or more emitter fiber optic fibers from a light source emitting in a first direction through at least a portion of the sensing region, and then travels in a second direction that is substantially opposite the first direction where it is received by one or more receiver fiber optic fibers. In other words the emitter fibers or the receivers can include a loop in the fiber.

The method can include a reference measurement within the sensing region. Typically, the analyte enters the reaction region through an analyte inlet and the analyte concentration is determined by using the signal from at least one oxygen probe that is sufficiently close to the analyte inlet to be sensitive to analyte-derived oxygen gradients within the sensing region along with the signal from at least a second oxygen probe that is sufficiently far from the analyte inlet to act as a reference probe for the oxygen profile. The reference probe can be sufficiently far from the analyte inlet so that the signal from the reference probe is not substantially affected by the analyte entering the analyte inlet.

In illustrative aspects, a spatially substantially uniform oxygen concentration is present at the boundary of the reaction region and the oxygen transport region. Furthermore, the oxygen transport region typically provides a sufficient oxygen flux to the reaction region such that the enzyme reaction is not oxygen limited. In addition, the size of the analyte inlet, the concentration of an enzyme in the reaction region, and the concentration of the reversible oxygen binding protein in the reaction region can be tuned to provide an analyte sensitive oxygen gradient near the inlet such that the desired dynamic range of analyte concentrations can be measured, and to provide a analyte insensitive oxygen reference concentration distal to the inlet.

BRIEF DESCRIPTION OF THE DRAWINGS

In FIG. 4B, separation is illustrated between the emitter bundle and the reaction region. However, in other aspects of the invention, the emitter bundle is in contact with, and butted up against, the reaction region.

DETAILED DESCRIPTION OF THE INVENTION

Figure 1:
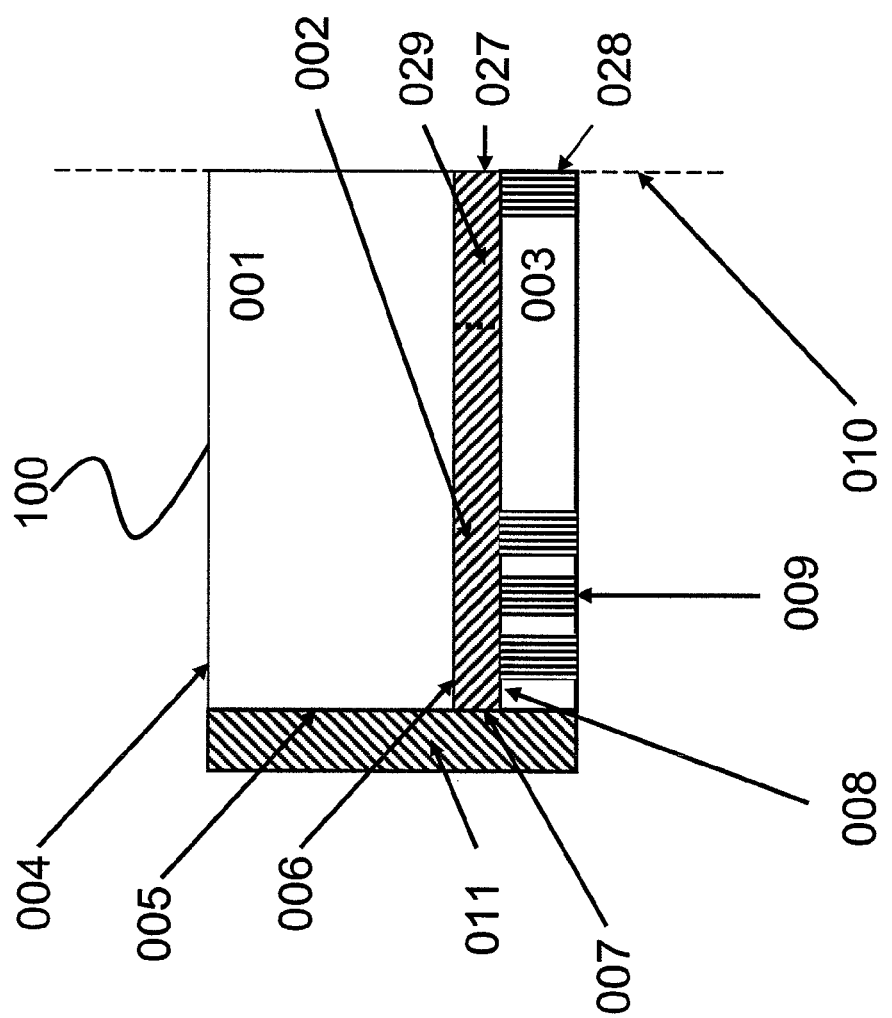
FIG. 1 provides a schematic drawing of glucose sensor geometry according to illustrative aspects of the present invention.

The present invention is based, at least in part, on the discovery that a reversible oxygen-binding protein, such as hemoglobin, can be used as an oxygen conduit in a stabilized oxygen transport matrix. The stabilized matrix collects oxygen, stabilizes oxygen dynamics, and rapidly transports oxygen away from a region of relatively high oxygen surrounding one surface of the stabilized matrix, to a region of lower or no oxygen on a second surface. The stabilized oxygen matrix provides numerous functions including rapid transport of oxygen in an implantable sensor and rapid transport of oxygen to an artificial tissue.

Accordingly, provided herein are biosensors, especially implantable glucose sensors, that utilize the stabilized oxygen transport matrix as an oxygen transport region and a reaction region to overcome challenges of implantable sensors, such as spatial and temporal changes in oxygen concentration at the site of an implant. The reversible oxygen-binding protein conduit can be used to increase the supply of oxygen to a selective mediator such as glucose oxidase in a homogenous, measurable manner. Furthermore, the oxygen binding protein within a stabilized oxygen transport matrix can be used to optically measure changes in oxygen concentration within regions of the matrix that result from the reactions within the matrix in which oxygen is consumed, such as a glucose-oxidase catalyzed reaction of glucose with oxygen.

In a first embodiment, the present invention provides a sensor that includes an oxygen transport region comprising a first reversible oxygen binding protein, an oxygen permeable first surface in communication with an external environment, and an oxygen permeable second surface which is impermeable to the target analyte; a target analyte reaction region in communication with the oxygen transport region at the oxygen permeable second surface, wherein the target analyte reaction region comprises a target analyte oxidase enzyme, and a target analyte-permeable surface and a sensing region comprising at least one detector probe in communication with the target analyte reaction region. Typically, a target analyte and oxygen impermeable surface is located in the sensor such that the sensing region is in between the target analyte and oxygen impermeable surface and the oxygen transport region. The sensing region is typically in optical, electrical, or molecular communication with the target analyte reaction region.

In certain aspects, the sensor includes an oxygen transport means for transporting oxygen from a surface in contact with an external environment to a target analyte reaction region and a detection means for detecting and/or measuring oxygen, the target analyte, or a product of the reaction of oxygen and the target analyte within a sensing region within the reaction region or contacting the reaction region. Numerous examples of the oxygen transport means and detection means are provided herein.

The first reversible oxygen binding protein can be, for example, an engineered hemeprotein or a heme derivative. In illustrative examples, the first reversible oxygen binding protein is myoglobin, or in further illustrative examples, hemoglobin.

Many different target analytes can be detected and measured by the sensors provided herein provided that the target analyte reacts with oxygen. For example, the target analyte can be galactose, lactose, peroxide, cholesterol, amino acids, alcohol, or lactic acid. In an illustrative example, the target analyte is glucose and the sensor is a glucose sensor. It will be understood that the teachings provided herein with respect to glucose can be used to make and use sensors for other analytes that react with oxygen.

Accordingly, as illustrated in FIG. 1, provided herein is a glucose sensor 100 that includes an oxygen transport region 001, that includes a reversible oxygen binding protein, an oxygen permeable first surface 004 and an optional oxygen permeable surface 005 in communication with an external environment, and an oxygen permeable second surface 006, sometimes referred to herein as the oxygen injector 006; a glucose reaction region 002 in mass transport communication with the oxygen transport region 001 at the oxygen permeable second surface, wherein the glucose reaction region includes, the reversible oxygen binding protein, a glucose oxidase enzyme and a glucose permeable surface 007, sometimes referred to herein as the glucose inlet 007, and a sensing region 003 in optical or electrical communication with the glucose reaction region 002, wherein the sensing region 003 includes a probe, such as an oxygen probe, a glucose probe, or a probe that binds to, or is otherwise affected by, a product of the reaction of oxygen and glucose. The sensing region 003 can be a region within the reaction region 002, or a region sufficiently in contact with the glucose reaction region to represent the spatial and temporal profile of glucose or other target analyte, oxygen, and/or reaction product within the reaction region, that is interrogated by one or more detector probes 009, which are individual sensing elements 009 within a sensing interface. Furthermore, the device can have an axis of symmetry 010. The oxygen transport region 001 is an exemplary stabilized oxygen transport matrix of the present invention. Communication between the oxygen transport region 001 and the glucose reaction region 002 typically occurs across a surface 006 where the oxygen transport region 001 and glucose reaction region 002 are in contact. The communication between the oxygen transport region 001 and the glucose reaction region 002 can be any type of communication that involves diffusion and permits the transport of oxygen from the oxygen transport region 001 into the glucose reaction region 002. The communication can be, for example, the movement of liquid, gas, and/or ions from the oxygen transport region 001 to the glucose reaction region 002.

In certain aspects of a sensor of the present invention, an outer membrane 011 can surround all or a portion of the device. The membrane is typically permeable to oxygen and glucose, but impermeable to at least some biomolecules such as proteins, especially biomolecules such as proteins within the sensor and of immune proteins. Therefore, the membrane has a cutoff, for example, of 1 kDa, 2 kDa, 5 kDa, 10 kDa, or 25. In some aspects, the membrane pores can be up to about 10 um, or the membrane can be laminar with an outer layer with pores up to 10 um to facilitate cell infiltration, and the inner layer can have pore sizes of as small as 10 kDa to prevent protein transport.

In another embodiment, provided herein is a method for measuring a concentration of an analyte, that includes transporting oxygen from an external environment through an oxygen transport region within a sensor to an analyte reaction region of the sensor using a first reversible oxygen binding protein; reacting a portion of the transported oxygen with the analyte enzymatically in the analyte reaction region to form a product; and measuring oxygen or a product of the reaction of oxygen and the analyte. The measuring is performed in a sensing region that includes the analyte reaction region or a sensing region in contact with the analyte reaction region. As discussed herein, virtually any analyte can be detected and measured using the methods herein provided that the analyte reacts with oxygen. In certain aspects, the analyte being measured is galactose, lactose, peroxide, cholesterol, amino acids, alcohol, or lactic acid. In illustrative aspects, the analyte being measured is glucose. It will be understood that the teachings with respect to measuring glucose can be applied to methods for determining virtually any analyte that reacts with oxygen.

Accordingly, provided herein is a method for measuring glucose concentration, that includes transporting oxygen from an external environment through an oxygen transport region 001 to a glucose reaction region 002 using a reversible oxygen binding protein, reacting a portion of the transported oxygen with glucose in the glucose reaction region 002 to form a product; and measuring oxygen, glucose, or a product of the reaction of oxygen and glucose in a sensing region 003 within the glucose reaction region 002 or in contact with the glucose reaction region 002, thereby measuring glucose concentration. In illustrative examples, oxygen is measured in the reaction region to measure glucose concentration.

In an illustrative aspect, a glucose sensor 100 provided herein is an implantable glucose sensor, for example a transcutaneous glucose sensor. Typically, transcutaneous glucose sensors can be removed by a user. Some sensors provided herein can be delivered as part of, or connected to a catheter, into a blood vessel. The methods provided herein measure relative or absolute concentrations of glucose in tissue, by transporting oxygen from tissue in the region around the sensor to the glucose reaction zone using an oxygen transport means. In illustrative aspects, the implantable sensor is implanted in subcutaneous tissue and oxygen is transported by the oxygen transporter to the reaction zone from tissue surrounding at least a portion of one side of the oxygen transporter, and typically all sides of the transporter except for the side that abuts the glucose reaction zone. In embodiments where the sensor is implanted in subcutaneous tissue, the sensor can be a subcutaneous sensor, but typically the sensor is a transcutaneous sensor in which a portion of the sensor traverses the skin of an animal, for example a mammal, such as a human. For example, probes connected to the sensor can traverse the skin to reach a light source and a detector that are located outside the body. In subcutaneous embodiments, the entire sensor as well as the detector can be located subcutaneously. The light source can be located subcutaneously, or an external light source can be used that is not physically connected to the sensor. The sensor can also be used to measure glucose concentrations as well in the vasculature, bodily excretions, or other tissues such as muscle, or fat, that may have higher or lower vascularization and oxygen tension than subcutaneous tissue.

The method and sensors provided herein can be used to monitor changes in absolute or relative glucose concentration. For example, diabetics can use the sensors and methods to monitor their glucose levels to determine whether changes in glucose concentrations are being adequately managed by a treatment regime. Furthermore, diabetics can use the sensor 100 in the control of insulin delivery. Therefore, methods provided herein typically include at least measuring glucose concentrations at a first time point and a second time point, thereby providing information regarding changes in glucose concentration over time. The devices and methods provided herein can be used to measure relative or absolute changes in glucose concentrations, with high sensitivity and precision across the entire range of at least 10 to 600 mg/dl which brackets the clinically relevant concentrations of 70 mg/dl and less which define hypoglycemia, and 250-400 mg/dl and up which define hyperglycemia. The device probes the spatial distribution of oxygen in a glucose reaction zone in which changes of oxygen concentration are used to infer changes of glucose concentration according to the kinetics of the glucose oxidase enzyme. Sensor calibration, which may include the oxygen reference measurement described herein, allows absolute glucose concentration measurements based on changes in the oxygen concentration distribution. Patients can be alerted by the sensor if their blood glucose falls below factory or user set concentrations, for example 90 mg/dl and/or if rates of glucose concentration decrease exceeds factory or user set rates, for example 10 mg/dl*$min^{-1}$ over a sustained period.

In certain illustrative examples, the sensors and methods provided herein are used to measure glucose concentrations on an ongoing basis, such as periodically at repeated time points (e.g., first, second, third, fourth, fifth, sixth, seventh, etc. time points) or continuously. Glucose measurements can be taken at virtually any interval, for example, in real time for continuous monitoring, or at intervals of less than a second, seconds, minutes, hours, or days. Continuous monitoring includes monitoring using pulsed light that is emitted into the sensing region at a relatively high frequency (e.g., once every 5 or 10 seconds with 1 to 5 second duration, or every one second with a 0.1-0.5 second duration). The sensors can be easily inserted beneath the skin, for example by simply holding the sensor housing, which may be a cylinder of 1 inch diameter and ½ inch thickness from which a needle protrudes within which is the sensor, and driving the needle through the skin into the subcutaneous tissue. Alternatively, the housing can be loaded into a spring-loaded device which is placed against the skin, and upon actuation of a lever or button, said device can insert the needle under the skin. The device can then remain in its transcutaneous or subcutaneous location for a period of hours, days, weeks, months, or even years, to allow periodic or continuous sensing of blood glucose levels.

A biosensor 001 according to the present invention typically utilizes a system designed around a reaction between a compound and oxygen that is mediated by an oxidase enzyme. As a specific embodiment, the enzyme glucose oxidase is used to catalyze the reaction of oxidizing glucose to gluconic acid and peroxide in the presence of water and oxygen.

$$C_6H_{12}O_6 + O_2 + H_2O \rightarrow C_6H_{12}O_7 + H_2O_2 \quad (1)$$

This reaction consumes both the desired analyte (glucose) and oxygen and creates products other than oxygen and the desired analyte. This reaction is dependent on both the analyte and the oxygen present at the catalytic site of the enzyme. Thus a glucose concentration is coupled to an oxygen reduction and new product concentrations. The sensor can then measure the concentration of glucose by measuring the reduction in the concentration of oxygen, glucose, or a product of the reaction of oxygen and glucose, as it is consumed or produced in the oxidase enzyme mediated reaction. This typically requires that a background oxygen measurement at the site of the glucose reaction be provided to interpret changes in the oxygen field.

Illustrative examples of biosensors provided herein are intended to operate under physiological tissue conditions, in which the availability of oxygen is significantly less than the availability of glucose. Intravenous sensor placement proximal to the heart has shown to be an excellent environment for long term glucose sensing in terms of oxygen availability and very limited rejection by the body. However, there are mortal risks associated with the intravenous placement making a non-vascular placement desirable since it is less invasive and does not pose some of the potential life threatening risks of the vascular implant site. Yet in subcutaneous tissues it has been shown that the tissue oxygen tension is quite low in comparison to atmospheric or arterial oxygen tension. Many tissues of the human body have an oxygen tension equivalent to between about 5% oxygen in nitrogen or lower, and there may be a ratio of glucose to oxygen sometimes as high as 100 to 1 in subcutaneous interstitial fluids.

As the glucose oxidation reaction (equation 1) requires equal molar amounts of oxygen and glucose, the reaction may be limited by a lack of oxygen. If bulk oxygen is considerably less available than bulk glucose (which is the norm in the subcutaneous environment), then the availability of oxygen to the catalytic site will govern the reaction rather than the availability of glucose. Under these conditions, the reaction chamber of the sensor is like a car engine that had the carburetor flooded with fuel, the combustion reaction in the engine will not proceed efficiently with too much fuel and not enough oxygen. The combustion reaction will still proceed but only to the extent that there is oxygen available as there is excess fuel. This limits the sensitivity of the sensing system to glucose.

To overcome the physical limitations of glucose, oxygen, and enzyme working within a simple unregulated solution, biosensors according to the present invention are constructed much like an engine. Within this analogy, the fuel is glucose, the spark plug is the catalytic site of the enzyme, and the oxygen is necessary for the reaction to proceed. This creates a transport and reaction problem. The goal is to get the balanced amounts of oxygen and glucose to the catalytic site of the enzyme. This will make the reaction at the enzyme responsive to changes in the glucose concentration, like a car engine is responsive to changes in the fuel flow controlled by the driver, and not to changes is ambient oxygen. Specifically, the biosensor is designed to have the reaction be sensitive to variations in the bulk glucose concentration and insensitive to transient variations in the bulk oxygen concentration.

The invention overcomes the issue of limited glucose sensitivity by implementing the necessary boundary conditions for the glucose oxidase reaction to readily occur. This is accomplished by rapidly transporting the needed oxygen to a reaction region 002 where the boundary conditions governing the glucose reaction are carefully regulated.

The reaction region 002 is formed from multiple boundaries (FIG. 1):

A boundary 006, also referred to herein as the oxygen injector, in the reaction chamber permitting high oxygen transport but no glucose transport.

A boundary 007, also referred to herein as the glucose inlet, permitting the entrance of glucose from the bulk into the reaction chamber juxtapose to the boundary 006. The boundary 007 may also allow oxygen to enter. The entire boundary 007 may be permeable to glucose or may contain an inlet or inlets that are permeable to glucose.

A boundary 008, called the sensing surface, that is impermeable to both glucose and oxygen allows sensing of the reaction chamber and is axially offset from the oxygen injector 006 and juxtaposed to the glucose inlet 007.

In addition to the three boundaries 006, 007, 008 delineating the reaction chamber, the complete sensor system contains an oxygen transport region 001 and a sensing region 003 contiguous with boundary 008. In certain aspects, the reaction region 002 is interrogated with a temperature probe. Readings from the temperature probe can be used in a determination of absolute concentration of glucose, due to the temperature dependence of the glucose oxidation reaction. The temperature probe can be an optical probe whereby infrared light is collected by a fiber optic or fiber optic bundle coupled to a pyroelectric detector located in the same housing as, and communicating with a signal processing unit. The temperature probe can be used as an input to the calibration for glucose concentration. It can communicate, for example, electronically with a signal processing unit.

Figure 5B:
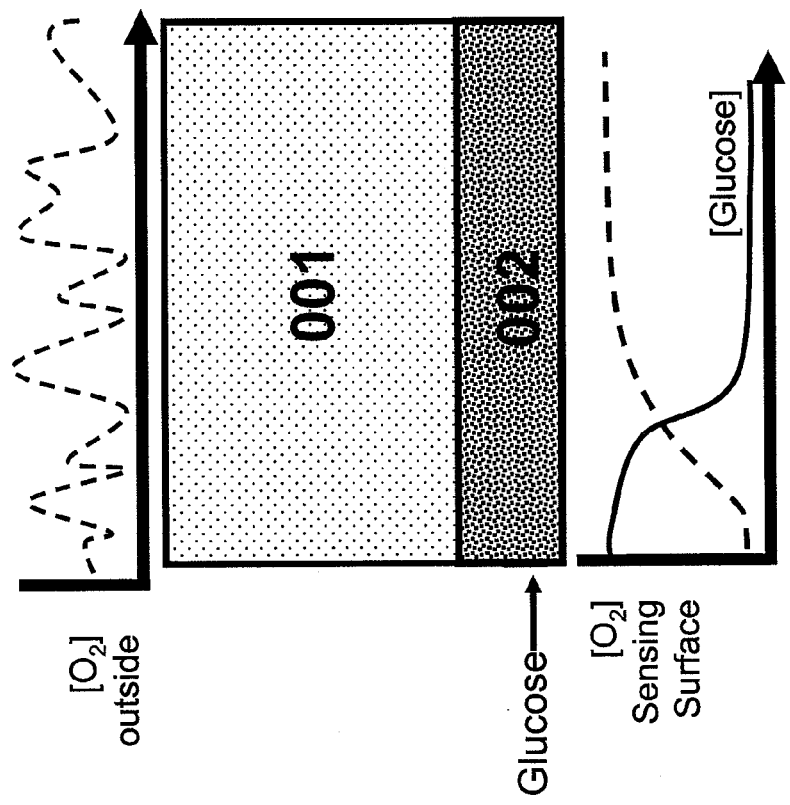
FIGS. 5A and 5B provide a schematic diagram and graphs illustrating expected oxygen and glucose concentration changes in a glucose sensor according to the present invention. The upper graph in FIGS. 5A and 5B represents expected spatial fluctuations in oxygen concentration in subcutaneous tissue outside the glucose sensor at the surface where oxygen enters the oxygen transport region 001 of the glucose sensor. The lower graph in FIG. 5A illustrates expected oxygen concentrations across the oxygen injector surface 6 and within the glucose reaction zone in the absence of glucose. The lower graph in FIG. 5B illustrates expected spatial changes in oxygen concentration (dashed line) and glucose concentration (solid line) across the glucose reaction zone 2 at a plane within the glucose reaction zone 2 after entry of glucose through a glucose inlet 7.
Figure 5A:
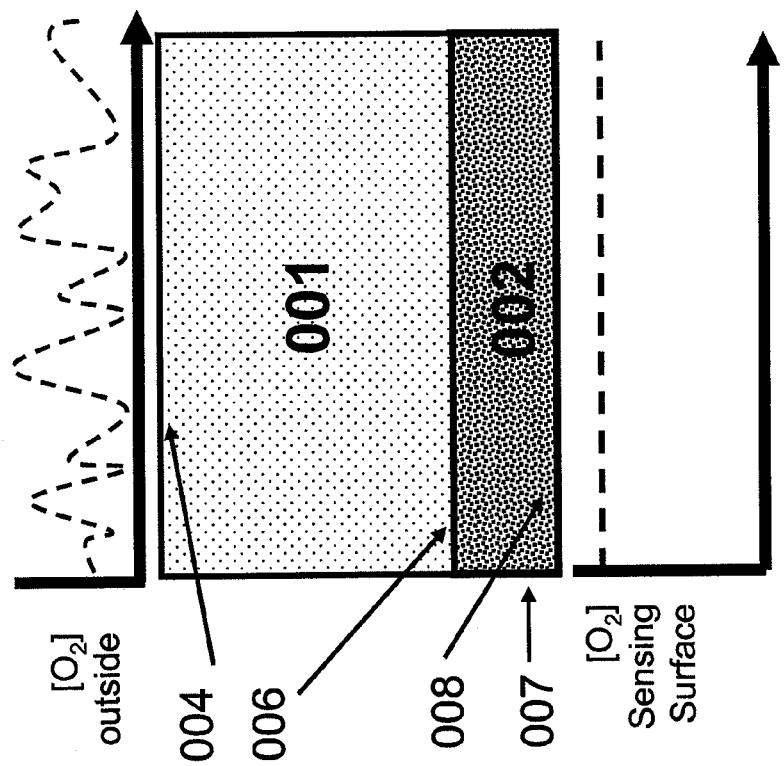

The oxygen transport region 001 is designed to collect oxygen, stabilize oxygen dynamics, and rapidly transport oxygen from an extended region away from the reaction chamber to the oxygen injection surface, named the oxygen injector,006, of the reaction chamber. Therefore, the oxygen transport region functions as an oxygen transport means. The oxygen transport region 001 provides a sufficient oxygen flux to the reaction region 002 such that the enzyme reaction is not oxygen limited. The sensing element optically interrogates the reaction chamber or subregion(s) of the reaction chamber to measure oxygen through boundary 008. FIG. 5A demonstrates the function of the oxygen transport region 001 whereby oxygen from a heterogeneous substantially non-zero oxygen field outside the first surface of the oxygen transport region is transported to the oxygen transport second surface 006 where it enters the reaction region 002 as a smoothed oxygen field as is represented by the graphical plots of oxygen concentration profiles '[$O_2$] outside', and '[$O_2$] sensing surface' (for the sake of illustration, the sensing surface 008 and surface 006 will have sufficiently equivalent profiles in the absence of glucose).

A "reversible oxygen binding protein" is a oxygen-carrying protein that reversibly binds oxygen under physiologically relevant oxygen concentrations. The reversible oxygen binding protein binds oxygen at some higher partial pressures and releases oxygen when oxygen concentrations fall, the change in the saturation of the protein as a function of the oxygen partial pressure being described by an oxygen saturation (also termed dissociation) curve. For example, the oxygen saturation curves of the reversibly oxygen binding proteins hemoglobin (haemoglobin) or myoglobin have very different loading and unloading characteristics as summarized by their strikingly different oxygen saturation curves. The hemoglobin saturation curve is sigmoidal, which reflects its cooperative binding, whereas that for myoglobin is hyperbolic which reflects noncooperative binding. Comparing the curves for hemoglobin to myoglobin, the saturation of myoglobin is always higher than hemoglobin at all partial pressures, indicating the higher affinity of myoglobin for oxygen than that of hemoglobin for oxygen. Consequently, in blood capillaries (partial pressure of oxygen is approx 20 mmHg) hemoglobin will release its oxygen to the tissues and allowing the myoglobin to store the oxygen for later releasing it to the tissues.

The reversible oxygen binding protein contains an oxygen binding site that is modulated by at least a peptide unit. For example, a heme group is modulated in hemoglobin or myoglobin. However, the reversible oxygen binding site may not employ a heme group as is the case for some hemoglobin orthologs. For example, the reversible oxygen binding proteins found in invertebrates such as hemocyanin found in mollusks and crabs arthropods which has two Cu ions for the reversible oxygen binding site, or Hemerythrin found in some marine invertebrate that also does not contain a heme group. The oxygen binding protein may also be synthetically derived with multiple functions such as the recombinant human serum albumin (rHSA) incorporating the synthetic heme "albumin-heme" to form an oxygen-carrying plasma protein (J Biomed Mater Res. 2004 Dec. 15; 71A(4):644-51), or such as the recombinant, human anti-sickling beta-globin polypeptide designated beta(AS3) (betaGly(16)-->Asp/beta-Glu(22)-->Ala/betaThr(87)-->Gln) was designed to increase affinity for alpha-globin (J Biol. Chem. 2004 Jun. 25; 279 (26):27518-24. Epub 2004 Apr. 14). Additionally, other genetic changes may be used to achieve different variants of reversible oxygen binding proteins, such as the *Escherichia coli* produced recombinant hemoglobin(alpha 29leueine-->phenylalanine, alpha 96valine-->tryptophan, beta 108asparagine-->lysine) which exhibits low oxygen affinity and high cooperativity combined with resistance to autoxidation (Biochemistry. 1999 Oct. 5; 38(40):13433-42.

The reversible oxygen binding protein in illustrative examples is present in the glucose reaction region (also called the glucose reaction zone) and/or the sensing region, as well as the oxygen transport region. The reversible oxygen binding protein is present in the oxygen transport region typically at a concentration of 0.1 g/dl-100 g/dl, for example 7.5 g/dl. The reversible oxygen binding protein can be increased or reduced in concentration until such a point at which the extraordinary oxygen transport rates, as illustrated in the Examples, are no longer achievable. The upper limit of the concentration of the reversible oxygen binding protein is also limited by the maximum ability to load the protein based on the mass of the protein.

The reversible oxygen binding protein in illustrative embodiments is a naturally occurring oxygen carrier, for example a heme derivative or a non-heme containing oxygen binding protein, or the reversible oxygen binding protein is an engineered hemeprotein. An engineered hemeprotein is a non-naturally occurring heme-based oxygen carrier or a modified naturally occurring heme-based oxygen carrier protein suitable for performing the function of the reversible oxygen-binding protein disclosed herein. The protein is typically engineered using recombinant DNA technologies. A heme derivative is a naturally occurring heme-based oxygen carrier such as an oxygen binding protein, which includes, for example, hemoglobin and myoglobin, or naturally occurring orthologs and variants thereof. In certain illustrative examples, the reversible oxygen binding protein is hemoglobin. The reversible oxygen binding protein typically undergoes relatively large changes in $O_2$ saturation with respect to small changes in $O_2$ partial pressure. For example, in transcutaneous sensor applications, the reversible oxygen protein can undergo relatively large changes in saturation in $O_2$ partial pressures up to at least, for example, 1, 2, 2.5, 3, 4, 5, 6, 7, 8, 9, or 10%, illustrative partial pressures in certain subcutaneous tissues. Accordingly, in methods provided herein oxygen is transported from the external environment to the glucose reaction zone using hemoglobin, myoglobin or an engineered heme-protein as the reversible oxygen binding protein. In illustrative embodiments, the reversible oxygen binding protein has a near linear saturation at oxygen pressures expected for the application of the sensor. For example, the reversible oxygen binding protein can have a near linear saturation response in $O_2$ partial pressures between 0 and 1, 2, 2.5, 3, 4, 5, 6, 7, 8, 9, or 10%, in transcutaneous sensors. In certain particularly illustrative examples, the reversible oxygen binding protein is hemoglobin at a concentration of between 1 and 25 g/dl, for example between 5 and 10 g/dl, or in an illustrative example at 7-8 g/dl, and even more particularly for example at 7.5 g/dl. Variants of hemoglobin are known within and between species. Furthermore, hemoglobin or engineered heme-proteins (Winslow R. M., .MP4, a new nonvasoactive polyethylene glycol-hemoglobin conjugate. Artif Organs. 2004 September; 28(9):800-6; Komatsu T, et al., Physicochemical characterization of cross-linked human serum albumin dimer and its synthetic heme hybrid as an oxygen carrier. Biochim Biophys Acta. 2004 Nov. 18; 1675 (1-3):21-31)) can be designed and produced using approaches such as recombinant DNA techniques (Leon R G, et al., High-level production of recombinant sulfide-reactive hemoglobin I from *Lucina pectinata* in *Escherichia coli* High yields of fully functional holoprotein synthesis in the BLi5 *E. coli* strain. Protein Expr Purif. 2004 December; 38(2):184-195) that may have normal or altered oxygen binding properties that are ideal for the biosensors provided herein, depending on the specific application of the biosensor. Additionally, the hemoglobin or engineered hemeprotein can be modified to attain different oxygen saturation curves suitable for delivery or improved measurement properties for a transcutaneous sensor operating at the expected low physiological oxygen tensions. Examples of modifications include crosslinking as part of the process to create the stabilized matrix with hemoglobin using gluteraldehyde or other agents to shift the p50 of the hemoglobin saturation curve. In the case of gluteraldehyde modification, the extent of the p50 shift will be dependent on the source of hemoglobin (e.g., human or bovine), the molar ratio of gluteraldehyde to hemoglobin and whether additional cofactors are included during crosslinking (Keipert, P. E., et al., Functional properties of a new crosslinked hemoglobin designed for use as a red cell substitute. Transfusion. 1989 November-December; 29(9):768-73; and Eike, J. H., Effect of glutaraldehyde concentration on the physical properties of polymerized hemoglobin-based oxygen carriers. Biotechnol Prog. 2004 July-August;

20(4):1225-32) In certain aspects, the oxygen transport region includes a series of bands each comprising a different engineered hemeprotein, myoglobin, hemoglobin variant, or hemoglobin, or combination thereof, with an altered oxygen saturation curve, such that reversible oxygen binding proteins in each band have different oxygen loading and/or unloading characteristics. Such a design can be used to fine tune the glucose sensor for a particular application.

It will be understood that although the sensor and methods provided herein are illustrated using the detection of glucose, the teachings herein can be used in sensors and methods for detecting other analytes as well. Accordingly, provided herein are methods and sensor devices for measuring an analyte, wherein the device includes an oxygen diffusion region that includes a reversible oxygen binding protein at a concentration sufficient to transport oxygen from one or more oxygen entry surfaces of the oxygen diffusion region to an analyte reaction zone that includes an oxidase enzyme that catalyzes the reaction of oxygen with the analyte. The device typically includes a sensor region for measuring the analyte, oxygen, or a product catalyzed by the oxidase enzyme. The device in illustrative examples, measures oxygen by measuring changes in absorption of the reversible oxygen binding protein (i.e. utilizes the reversible oxygen binding protein as both an oxygen transporter and an oxygen probe). Virtually any analyte can be measured using the inventive sensors and methods where oxygen can be used as a co-factor for an enzymatic reaction involving the analyte, and $O_2$ is not present upon completion of the enzymatic reaction. In addition to glucose oxidase, as illustrated herein, other analytes that can be measured include galactose, using galactose oxidase, lactose, using lactose oxidase, peroxides, using peroxidases, cholesterol using cholesterol oxidase, amino acids using amino acid oxidase, alcohol using alcohol oxidase, and lactic acid using lactate oxidase.

The characteristics of a reversible oxygen binding protein can be analyzed with respect to the illustrative reversible oxygen binding protein hemoglobin. The nonlinear loading and unloading characteristics of hemoglobin and myoglobin greatly facilitate the transport of oxygen from the bulk through the oxygen transport region 001 and into the reaction chamber via the oxygen injector 006. The transport characteristics of hemoglobin move the oxygen through the oxygen transport region 001 to the low oxygen tension regions at a speed far in excess of normal diffusion. This extremely rapid transit coupled with the unique loading and unloading characteristics of hemoglobin create a spatially substantially uniform or self-consistent distribution identifiable by the oxygen reference value across the profile of the oxygen transport region 001 at the injector surface 006. Additionally, these unique loading and unloading characteristics buffer variations in the oxygen supply being transported through the oxygen transport region 001. A value at the reference should map to the same oxygen distribution regardless of the distribution outside the first surface of the oxygen transport region. Here 'map' is intended to mean that a reference value codes for only one oxygen distribution across the injector. While a nonspatially uniform injector oxygen field or profile may result in a nonmonotonic oxygen field in the glucose reaction zone which may be compensated for in an appropriate calibration, a spatially substantially uniform injector oxygen field or profile provides a simpler oxygen to glucose calibration. Therefore, the oxygen transport region 001 provides a temporally substantially damped oxygen concentration profile with respect to bulk oxygen dynamics at the boundary 006 of the glucose reaction zone 002 and the oxygen transport region 001. These unique characteristics allow the conduit 001 to stretch far into the bulk tissue environment, effectively uniting a supply of oxygen from capillaries and arterioles to the reaction region 002 where it is needed for the enzyme mediated oxidative reaction. The extensive oxygen collecting area of the oxygen transport region, 001 moves oxygen to the small volume of the reaction region 002 supplying ample oxygen for the glucose oxidase reaction. In this sense, the oxygen transport region 001 acts as an artificial microcirculation which couples the reaction region 002 to the microcirculation of the tissue.

The oxygen conducting potential of the oxygen transport region 001 also ameliorates another key roadblock in short term subcutaneous sensing. Numerous attempts have been made to make subcutaneously implanted devices for measuring glucose in diabetics. However, experimental devices have ultimately failed due to a lack of sensitivity to glucose after implantation. The lack of sensitivity has been ascribed to among other issues, the isolation of the biosensor electrode by layers of scar-like tissue. The scale and biocompatible composition of the exterior of the oxygen transport region 001 should allow it to remain proximal to arterioles and numerous capillaries. This should allow sufficient oxygen to remain transported to the sensing site even if the device is encapsulated. Accordingly, the implantable glucose sensor 100 of the present invention in certain illustrative embodiments, may contain a vast array of different geometrical arrangements of the key sensor components which will yield a functioning device. In certain aspects the geometry can be, for example, a cylinder no more than 100, 200, 300, 400, 500, 600, 700, 800, 900, 1000 $mm^3$ in total volume. For example, in embodiments where the implantable glucose sensor is cylindrically shaped, the diameter of the implantable glucose sensor in certain aspects is no more than 3.4 mm, 0.64 mm, or 0.31 mm. In certain embodiments the diameter of the implantable glucose sensor is the diameter of a 18, 23, or 30 gauge hypodermic needle. In an illustrative embodiment, the diameter can be as small as 0.030 mm and as large as 0.31 or 0.64 mm where the smallest represents the implantation of a single fiber optic probe and the largest represents fiber optic bundles implanted in a syringe needle ranging in gauge from 30 to 23. The length of the implantable glucose sensor can be, for example, between 1 mm and 100 mm, or in certain preferred illustrative examples, it is between 2 mm and 10 mm where length is a trade off between oxygen collection and comfort.

Accordingly, the lengths of the various boundaries and regions with the sensor provided herein are small enough to permit the sensor to have the overall total dimensions provided above. For example, the oxygen injector 006 can be, for example, between 0.05 and 10 mm, 0.1 and 1 mm, or between 0.1 and 0.3 mm in length. The glucose inlet 007 is typically between 0.0001 and 1 mm, or in illustrative examples, between 0.001 and 0.1 mm in length. The sensing surface 008 can be, for example, between 0.05 and 10 mm in length, and in illustrative examples is between 0.1 and 0.3 mm in length. The ratio of the length of the oxygen injector 006 to the length of the glucose inlet 7, is typically between 1 and 1000, and in an illustrative embodiment, is between 5 and 100, or more specifically between 6 and 30. However, it will be recognized that the biosensors provided herein are scalable and may take on various shapes. The glucose inlet is small enough to assure that a subregion within the reaction region 002 has no detectable glucose. In certain aspects, a characteristic length of the glucose inlet, defined as the square root of its area, is no more than ½ of a characteristic length of the glucose reaction region where the characteristic length is defined as the distance from the glucose inlet to the effective boundary of the glucose reaction region in a direction pointing along the surface normal of the glucose inlet. With respect to ratios of other regions of the sensor of the present invention, the length of the oxygen injector 006 can be, for example, approximately identical, or identical to the length of the sensing surface 008. The ratio of the volume of the oxygen transport region 001 and the volume of the reaction region 002 is typically at least 2:1, and in illustrative aspects is 5:1, 10:1, 100:1, 250:1, 500:1, or 1000:1. In preferred embodiment ratios of at least 5:1, and as high as 200:1 may be implemented where 200:1 represents a 0.050 mm thick reaction region 002 with a 10 mm oxygen transport region 001.

The oxygen transport region 001 in certain examples has a cross-sectional area of between 0.005 and 1 $mm^2$, or in an illustrative embodiment is between 0.015 and 0.08 $mm^2$, the inner diameter cross sectional areas of the 30 and 23 gauge needle respectively, and the glucose reaction region 002 typically has a matching cross sectional area along the axis of the oxygen transport region 001, as does the sensing region 003, in certain aspects. The sensing region in certain examples, has a slightly reduced cross-sectional area compared to the oxygen transport region. In aspects where the glucose inlet 7 is a circular hole, the diameter can be between 1 um and 1 mm, but it will be understood that the length of the glucose inlet 7 regardless of shape can be as large as the distance from the oxygen injector 006 to the sensing surface 008. The glucose reaction region 002 typically has a matching cross sectional area along the axis of the glucose inlet 007 of between about 10 um and 1 mm, for example between 25 um and 250 um, or in certain illustrative examples about 100 um. Not to be limited by theory, it is believed that the large ratios between cross-sectional areas along the axis of the oxygen transport region 001 and along the axis of the glucose inlet 007 (and of the glucose inlet itself), account for at least part of the sensor's ability to operate in low oxygen environments.

Within the reaction region 002, also referred to as a reaction zone or a reaction chamber, a means for rapidly transporting oxygen from the oxygen transport region boundary (i.e. oxygen injector) 006 into the reaction region and to the catalytic sites of the enzymes in the reaction region is provided. This can be accomplished again by employing a reversible oxygen binding protein such as hemoglobin, myoglobin, or an engineered hemeprotein to decrease the resistance to oxygen transport from the oxygen injector surface into the catalytic sites of the glucose oxidase enzyme. Additionally, the presence of a reversible oxygen binding protein within the reaction region will also decrease the diffusivity of glucose, helping to regulate the reaction by decreasing the flow of glucose down the established gradient in the reaction region 002, as discussed in more detail below. The net result is that the enzymatic reaction remains responsive to changes in bulk glucose concentration over a broad range of bulk glucose concentrations, and that the reaction couples bulk changes in glucose concentration to changes in the oxygen field in the reaction zone.

In certain aspects, the reversible oxygen binding protein within the oxygen transport region 001, and/or the reversible oxygen binding protein and the glucose oxidase in the glucose reaction region 002 can be placed in a stabilized emulsion to ensure high availability of the oxygen carriers to the catalytic sites of the enzyme in the reaction zone. For example, the stabilized emulsion can be a stabilized matrix.

The teachings herein with respect to an oxygen transport region 001 and a reaction region 002 of a biosensor 100, are applicable more generally to any method or device for rapidly transporting oxygen from a region of relatively high oxygen partial pressure to a region of lower partial pressures, as illustrated in the Examples provided herein. This general applicability is especially true for aspects of the invention where the oxygen transport region and/or the reaction region are stabilized matrices. The transport typically occurs without convection. Accordingly, provided herein in another embodiment, is a stabilized oxygen transport matrix that includes a reversible oxygen binding protein immobilized in the stabilized oxygen transport matrix. The reversible oxygen binding protein is typically stabilized throughout the matrix. However, as indicated herein, the concentration of the reversible oxygen binding protein can change within the matrix.

The stabilized matrix collects oxygen, stabilizes oxygen dynamics, and rapidly transports oxygen within the matrix. For example, the stabilized matrix can transport oxygen from a region of relatively high oxygen surrounding one surface of the stabilized matrix, to a region of lower or no oxygen on a second surface. Furthermore, the stabilized matrix can transport oxygen to a site within the matrix or juxtaposed to the matrix, where a reaction occurs in which oxygen is consumed, as illustrated by the reaction region 002 in the glucose sensors provided herein. In illustrative embodiments, the reversible oxygen protein, as indicated herein for other embodiments of the invention, is hemoglobin, myoglobin, or an engineered hemeprotein.

The stabilized oxygen transport matrix can take on virtually any shape or form provided that at least 1 surface of the oxygen transport region is permeable to oxygen and either a second surface is permeable to oxygen or oxygen is consumed at a region within the stabilized oxygen transport matrix. For example, the matrix can be one or a series of sheets or cylinders.

The stabilized oxygen matrix can include a variety of components in addition to the reversible oxygen binding protein, as disclosed herein with respect to an oxygen transport region 001 and a reaction region 002 of a sensor 100. For example, the stabilized matrix can include a carrier protein to protect protein function during matrix stabilization and during sensor operation. The carrier protein in certain illustrative embodiments is serum albumin and/or gelatin. It has been reported that adding the carrier protein at 1 to 15% by weight of final concentration will protect protein function (U.S. Pat. No. 6,815,186), especially for relatively low enzyme loadings, typically equal to, or less than, 70% by final concentration. In certain aspects, the loading can be as high as 15 g/L to 25 g/L at final concentrations. Stabilization of the matrix can be achieved, for non-limiting example, through crosslinking by at least one of the following agents: an aldehyde such as glutaraldehyde or formalin, a carbodiimide, an imidoester, a pyrocarbonate, an epoxide or N-hydroxysuccinimid ester. In certain aspects, the stabilized matrix contains the enzyme catalase or peroxidases in order to decrease the peroxide levels within the matrix. In certain aspects the catalase loading can be 1 to 20 units/ml (See e.g., glucose oxidase formulations available from Biozyme, United Kingdom) or 100 to 1000 units/mil; and U.S. Pub. Pat. App. No. 2002/0006634). Furthermore, the stabilized oxygen matrix can include polyglycolic acid (PGA), polylactic acid (PLA), poly(lactic-co-glycolic acid) (PLGA), PLLA, poly(caprolactone) (PCL), poly(dioxanone) (PDS), or neovascularization promoting-fibrous capsule inhibiting material such as polytetrafluoroethylene (PTFE), expanded polytetrafluoroethylene (ePTFE), polypropylene, and polyvinyl alchohol (PVA). These components can be used to stabilize reversible oxygen binding protein within the oxygen transport matrix. The reversible oxygen binding protein concentration can be as little as 10% by mass within the polymer, or in certain examples using polyethyleneglycol as the polymer, on the order of 5 to 200 parts reversible oxygen binding protein to polymer, and still retain its oxygen carrying characteristics (See e.g., Wettstein et al, "Resuscitation with polyethylene glycol-modified human hemoglobin improves microcirculatory blood flow and tissue oxygenation after hemorrhagic shock in awake hamsters", Crit. Care Med 2003 Vol. 31, No. 6; Moore, "Blood Substitutes: The Future Is Now", J Am Coll Surg., Vol. 196, No. 1, January 2003 and U.S. Pat. No. 5,585,484), incorporated herein in their entirety by reference. The stabilized oxygen matrix can include silicon or can be covered with a coating of silicon, rubber, or a polymer. Furthermore, in certain aspects, all or a portion of the stabilized oxygen transport matrix can be encapsulated by a membrane, such as a non-natural membrane made of, for example, a hydrophobic material such as silastic. In certain aspects, the stabilized oxygen transport matrix includes a reversible oxygen binding protein immobilized in the stabilized oxygen transport matrix within the pores of a permeable membrane. The membrane can be made virtually any type of membrane material, but in certain aspects, it is a biocompatible membrane that can be implanted in an animal, especially a mammal such as a human. In certain aspects the membrane material can be a naturally derived material such as, but not limited to, collagen, alginate, agarose, hyaluronic acid derivatives, chitosan, fibrin glue, or a synthetic polymer such as polyglycolic acid (PGA), polylactic acid (PLA), poly(lactic-co-glycolic acid) (PLGA), PLLA, poly(caprolactone) (PCL), poly(dioxanone) (PDS), or neovascularization promoting-fibrous capsule inhibiting material such as polytetrafluoroethylene (PTFE), expanded polytetrafluoroethylene (ePTFE), polypropylene, and polyvinyl alcohol (PVA).

In a related embodiment, provided herein is a method for transporting oxygen from a first area having a relatively high oxygen concentration to a second area having a relatively low oxygen concentration, that includes contacting oxygen from the first area, to a first surface of a stabilized oxygen transport matrix that includes a reversible oxygen binding protein immobilized throughout the stabilized oxygen transport matrix, and transporting oxygen away from the first surface of the stabilized oxygen transport matrix to a second surface of the oxygen transport matrix, wherein the second surface of the oxygen transport matrix contacts the second area. The reversible oxygen transport matrix is an example of an oxygen transport means. Transport of oxygen from an oxygen transport region 001 to a reaction region 002 of a sensor 100, is an illustrative example of this embodiment.

In yet another related embodiment, provided herein is a method for transporting oxygen from a first area having oxygen to a reaction area, that includes contacting oxygen from the first area, to a first surface of a stabilized oxygen transport matrix that includes a reversible oxygen binding protein immobilized throughout the stabilized oxygen transport matrix, and transporting oxygen away from the first surface to the reaction area, wherein oxygen is consumed in a reaction at the reaction area. Transport of oxygen within a reaction region 002 of a sensor 100 from a site of relatively high oxygen concentration away from a glucose inlet to a site of glucose closer to the glucose inlet, is an illustrative example of this embodiment. Methods of the present invention can be used to transport oxygen over distances from between 0.001 mm and 20 mm, for example between 0.01 mm and 0.5 mm, The stabilized oxygen matrices provide numerous functions including not only rapid transport of oxygen in an implantable sensor, but also rapid transport of oxygen to an artificial tissue. As such, the stabilized oxygen transport matrices provided herein can be used as oxygen delivery systems for artificial organs or cell/tissue transplants. The stabilized oxygen matrices are important to achieve desired responses of the transplant such as, but not limited to, viability, differentiation, and function, depends upon oxygen availability. In fact, one or more stabilized oxygen transport matrices can be part of an artificial microvasculature, a specific type of oxygen transport region used to collect oxygen from regions of high partial pressures distal from an implant and unloading the oxygen to the implant where oxygen partial pressure is lower. In these embodiments, the stabilized oxygen transport matrices can form a spider-like assembly of oxygen transport regions or a reticulated meshwork of matrices, in order to maximum the surface area of the stabilized oxygen transport matrix that contacts tissue regions that have oxygen.

Artificial microvasculatures composed of stabilized oxygen transport matrices provided herein can also be used to deliver oxygen to endogenous tissues, for non-limiting example, in a disease state, in treatment of cardiovascular disease, in wound healing, in treatment of cerebral hypoxia or hypoxic encephalopathy, or in limb reattachment after amputation. Other applications include supplying oxygen to tumors to prevent hypoxic-mediated radio and chemo resistance, the treatment of medical conditions linked to hypoxia such as rheumatoid and other types of arthritis, chronic inflammatory bowel disease, skin conditions such as eczema and psoriasis, diabetic inflammatory vasculopathy and diabetic neuropathy, and tendon degeneration.

Biosensors of the present invention, in certain illustrative aspects, utilize the discovery that an optical method can be coupled with a selective mediator such as glucose oxidase to develop a glucose sensor that will operate accurately in the subcutaneous tissues. The oxygen-sensing component of the biosensor is achieved by interrogating the oxygen field within the reaction region 002. This is accomplished electrically or optically, in which volumes of the reaction region 002 bound by the oxygen transport region boundary 006 and the sensing boundary 008 are sampled by one or more detector probes. FIG. 5B illustrates the transformation of the oxygen profile from a relatively uniform profile as shown in FIG. 5A in the absence of glucose, to a substantially non-uniform profile upon the entry of glucose through the inlet. As is illustrated in the figure, glucose at the inlet reacts with the oxygen, as mediated by the enzyme glucose oxidase, whereby oxygen is consumed. The oxygen consumption determines an oxygen profile within the reaction region which is detectable within the sensing region, which is dependent upon the concentration of glucose, the enzyme loading, and the oxygen flux at the injector surface (for any given device geometry of this invention). By design, the oxygen profile distal to the glucose inlet is sensitive to the injector oxygen concentration and not to the glucose concentration and can be used as an input to map the oxygen profile to a given glucose concentration. The detector probes, in illustrative aspects, are a series of substantially non-oxygen consuming probes which in certain aspects will consume less that 10% of the oxygen within the sensing region per characteristic time in which the characteristic time is the 95% rise time for the oxygen concentration within the sensing region following a step change of oxygen concentration at its boundary with the reaction region, or in certain aspects, with the injector surface. In other aspects, the characteristic time may be defined as the 95% rise time of oxygen concentration within the sensing region following a step change of glucose concentration at the glucose inlet. The detector probes typically are light conduits that collect light from one end and efficiently guide it to a second end. Emitters are detector probes that emit the light that interacts with an oxygen-sensitive media within the reaction region 002. Receivers recollect light that contacts the oxygen-sensitive media, for analysis. Therefore, emitters and receivers form a detection means. For example, the detector probes can be fiber optic fibers, fiber optic bundles, or light guides including liquid light guides. However, the detector probes in certain aspects, are substantially non-oxygen consuming electrodes that measure oxygen or a product of the reaction through a polarographic sensing system. In other aspects, one or more amperometric probes are used as detector probes to measure oxygen or a product of the reaction of oxygen and an analyte such as glucose, using an amperometric method. The amperometric method typically does not consume oxygen but consumes a product of the enzyme reaction between the target analyte and oxygen. In certain aspects, the one or more detector probes are peroxide electrodes. Peroxide is a product of a glucose oxidase catalyzed reaction. The peroxide electrodes can be used in conjunction with an oxygen reference which could be polarographic or optical or any substantially non-oxygen consuming probe. The depth of the interrogation can be adjusted. Furthermore, in illustrative examples, the region is spatially sampled with more than one light path to provide greater precision in monitoring changes in the oxygen field of the reaction zone. Oxygen, glucose, or a product of the reaction of oxygen and glucose can be detected.

As a reversible oxygen binding protein such as hemoglobin is present throughout the reaction region 002, it can serve as both an oxygen transporter and an oxygen probe. In other words, both the first reversible oxygen binding protein, an exemplary oxygen transporter, and the second reversible oxygen binding protein, an exemplary oxygen probe, can be hemoglobin. Therefore, in certain aspects the oxygen probe is an optically sensitive molecule, for example an engineered hemeprotein or a heme derivative, such as hemoglobin. In other aspects, the oxygen probe is an optical probe such as a dye, which depending on the specific dye used, can consume oxygen. The optical means of measuring the oxygen saturation of hemoglobin are well established, allowing oxygen concentration to be measured optically in a sensitive and selective fashion. This provides measurements of oxygen concentration, through and if needed outside of the enzyme reaction zone. Accordingly, in certain illustrative examples, the probes emit and receive light at an oxygen sensitive hemoglobin absorption wavelength, or an oxygen sensitive absorption wavelength of another reversible oxygen binding protein. An oxygen sensitive hemoglobin absorption wavelength is a wavelength belonging to the subset of the wavelengths of the hemoglobin absorption spectrum for which absorption is a function of hemoglobin oxygen saturation. Where hemoglobin is used as the reversible oxygen binding protein the detector probes emit and receive light at between 600 and 800 nm. Wavelengths greater that 800 nm also have the favorable properties of low absorption and of changes in the absorption with oxygenation. Wavelengths shorter than 600 nm have very high absorption and are less suitable for measuring oxygenation due to poor light throughput. For the device illustrated in the Examples herein, 635 nm was chosen for its low cost and ubiquitousness in the manufacture and industry of silicon chips, optoelectronics and integrated circuits. Two other working wavelengths include, for example, 660 nm or 905 nm, which are commonly used to measure hemoglobin oxygenation. A second wavelength can be used in addition to a primary wavelength to improve calibration stability. In particular the isobestic wavelength of hemoglobin, 805 nm, can be used to provide an oxygenation independent measurement which is effected by and provides a measurement of the amount of hemoglobin encountered in the light path.

The issues of selectivity are overcome by biosensing methods and biosensor devices provided herein, when a background oxygen measurement is taken at a region in the glucose sensor that is distant from a site 007 where glucose enters the sensor, but having an oxygen concentration that is similar to that initially present at the site where glucose enters the device. Accordingly, to further deal with the issue of sensitivity and dynamic sensing range, three surfaces 006, 007, and 008 of the reaction region 002 are designed to create a glucose gradient along the sensing boundary 008, which is also created by the very high lateral spatial normalization of oxygen of the oxygen transport region. Accordingly, at a point along a sensing boundary 008 in the reaction zone all of the measurable glucose has been converted to product, while at the glucose entrance boundary 007, the glucose concentration is higher. This design causes glucose to be drawn down a concentration gradient from the glucose entrance boundary 007 towards the center of the reaction chamber. Consequently there is an oxygen gradient in the reaction chamber since it is consumed along with glucose by glucose oxidase. When this oxygen field is spatially interrogated by the optical sensing elements, the result is a profile that is dependent on the bulk glucose concentration. The result is that the enzymatic reaction remains responsive to changes in bulk glucose concentration over a broad range of bulk glucose concentrations, and this reaction couples bulk changes in glucose concentration to changes in the oxygen field in the reaction zone.

The composition of the reaction region 002 is designed to contain sufficient glucose oxidase and reversibly oxygen binding protein so that as glucose moves from the glucose inlet 007 through the reaction region 002, its concentration is reduced such that at a point along the reaction region 002 away from the glucose inlet 007, the glucose concentration is reduced to a level that does not measurably reduce the oxygen concentration even in the presence of glucose oxidase. The reference region 029 is the region within the reaction region 007 where the glucose concentration is sufficiently low so as not to measurably reduce oxygen concentration in the reference region 029. The precise start of the reference region 029 within the reaction region 002 depends on the reaction rate of glucose near the glucose inlet 007 which will setup how deep the oxygen gradient extends. This is controlled by design via glucose oxidase loading, reversible oxygen binding protein concentration, size of the glucose inlet 007, area of the reaction zone 002, and the surface area ratio of the oxygen injector 006, to the glucose inlet 007. Therefore, the reference oxygen measurement aspect of the present invention is tunable and scalable. In certain aspects, the concentration of an enzyme in the reaction region 002, and the concentration of the reversible oxygen binding protein in the reaction region 002 are tuned to provide an analyte sensitive oxygen gradient near the inlet 007 such that the desired dynamic range of analyte concentrations can be measured, and to provide a analyte insensitive oxygen reference concentration distal to the inlet. The reference region is at least large enough to encompass a region of the reaction region 007 interrogated by one or more reference emitters and/or one or more reference detectors. A reference region 029 is located within the reaction region 002. The reference region 029 for example, can extend in certain aspects, from the center of the reaction region 007 with respect to a plane extending from the glucose inlet 007 to a distal boundary 027 of the reference region, and can extend through the distal boundary 027. In certain aspects, for example, the reference region can begin about 200 microns or so from the glucose inlet.

One or more reference detector probes 028, such as one or more reference emitter fiber optic bundles, can emit light into the reference region 029. For example, the reference probes can be located at least ½, ⅔, or ⅘ the total length of the reaction zone from the glucose inlet. In certain embodiments, the furthest 1, 2, 3, 4, or 5 fiber optic bundles or adjacent pairs of fiber optic bundles, in an array of emitter fiber optic bundles can be the reference emitter fiber optic bundle. Therefore, light can be emitted from one or more reference fiber optic bundles to excite an oxygen binding probe, such as hemoglobin, and absorption or emission of light from the oxygen-binding probe can be detected by one or more detector fiber optic bundles. This availability of the background measurement for oxygen within the reaction zone is useful, as it provides a highly relevant background measurement for the oxygen availability to the enzyme without disturbing the reaction occurring in the reaction zone. The reference measurement can be used to determine absolute or relative analyte concentrations, and it can provide a measure that can be used to map an oxygen profile in the reaction chamber In certain illustrative embodiments the emitters 410 and/or the receivers 415 are fiber optic fibers. In one implementation of this design, the sensing boundary 008 is the end of a fiber optic bundle. The resulting surface satisfies the requirement of a no flux boundary condition. The diameter of the fiber optic bundle can be, for example, between 100 um and 300 um. In certain aspects, the receiver, sometimes referred to as a receiver optrode, or the emitter, sometimes referred to as an emitter optrode, is a shaped fiber optic fiber. Typically, the sensor includes at least 2 receivers and/or emitters. This allows the spatial sampling of the reaction zone 002 disclosed herein, which can be performed using more than one receiver, more than one emitter, or more than one receiver and emitter. In certain aspects, the receiver is a miniaturized electronic optical receiver. The detector probes, such as the fiber optic fibers or fiber optic fiber bundles, can be coated with a bioadhesive molecule that increases the adhesion of biomolecules to the fiber or fibers. For example, the detector probes can be coated with polylysine. The bioadhesive molecule serves to increase the adhesion of the matrix of the reaction region 002 to the detector probe. In certain examples, the emitter and for detector are miniaturized electronics housed within a housing of the sensor, in which case no fiber optics are used. The physics of the measurement for these examples is the same as where fiber optics is used, but the method of interrogation could change, as will be understood. In one aspect, fused fiber bundles (also called imaging conduits) can be used. For example, fused fiber bundles that have a 50 um outer diameter, but contain an array of fused fibers within it, each, for example, 10 um in diameter. In this aspect, the reaction region can be sampled with a resolution of 10 um or less.

In one illustrative glucose sensor that utilizes fiber optic fibers, a biocompatible hollow micro-pore membrane tube, such as a micro porous hollow fiber membrane 11 permeable to glucose surrounds the tip of the optical fiber bundle and extends beyond the optical fiber bundle. The hollow micropore fiber membrane 11 covers the glucose entrance boundary 007 (i.e., glucose inlet). The reaction chamber 002 is then formed by placing a mixture of glucose oxidase, bovine serum album, and glucose, and oxygenated hemoglobin inside the hollow micro fiber membrane 11 and on the surface of the optical fiber bundle 008. The mixture is filled to a thickness of 50 um and is then cross-linked using glutaraldehyde. Liquid medical grade silicone is then added to hemoglobin in a quantity sufficient to form a suspension that will fill the hollow micro fiber membrane 11 creating the oxygen transport region 001 and contacting the exposed surface of the reaction chamber 002 to form a boundary 006.

Sensing then occurs in this illustrative glucose sensor by directing laser light through subregions of the optical fiber bundle to interrogate the reaction chamber oxygen field by monitoring the hemoglobin oxygen saturation. This light is then reflected at the oxygen injector 006 back through the optical fiber bundle and measured by a photodiode.

Figure 3A:
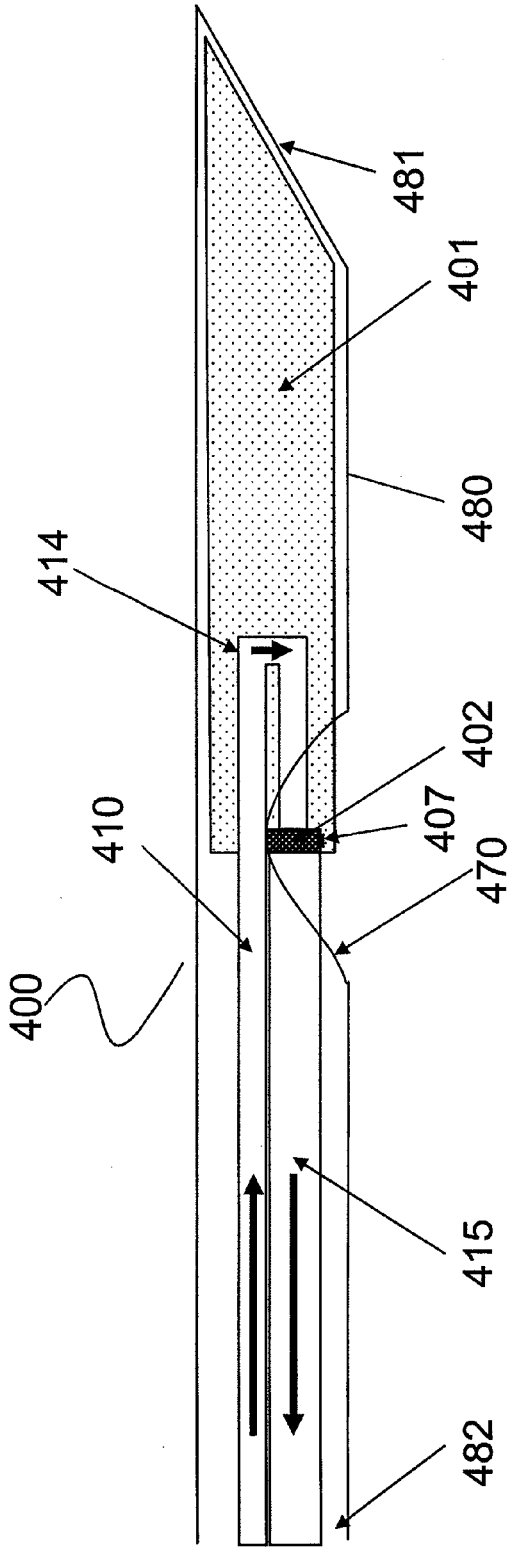
FIG. 3A provides a schematic drawing of an illustrative example of a glucose sensor of the present invention, as disclosed in Example 2.
Figure 3B:
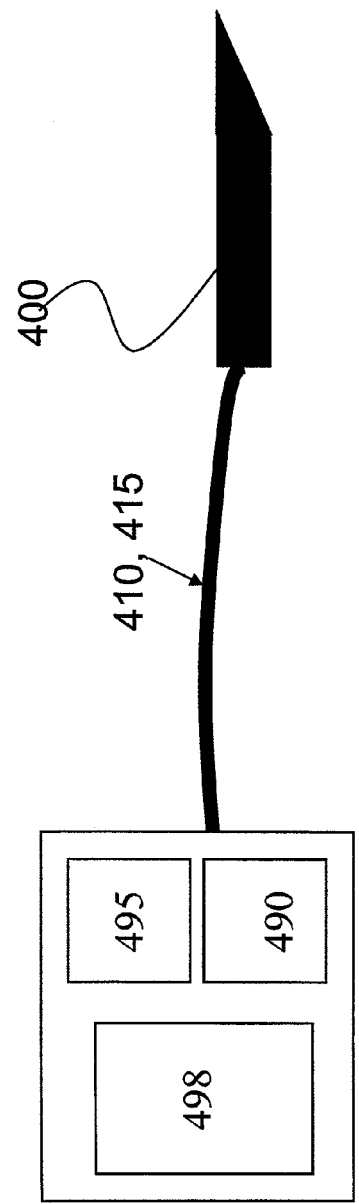
FIG. 3B provides a schematic diagram of the illustrative glucose sensor of Example 2 connected to a light emitter 490, light detector 495, and signal processing 498 unit.
Figure 4A:
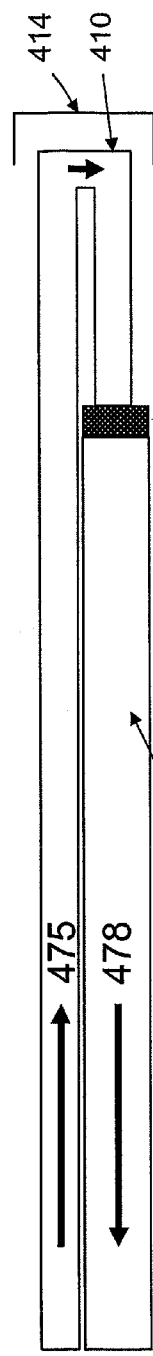
FIG. 4A provides a schematic drawing illustrating the path of fiber optic bundles and light in an illustrative glucose sensor of the present invention.
Figure 4B:
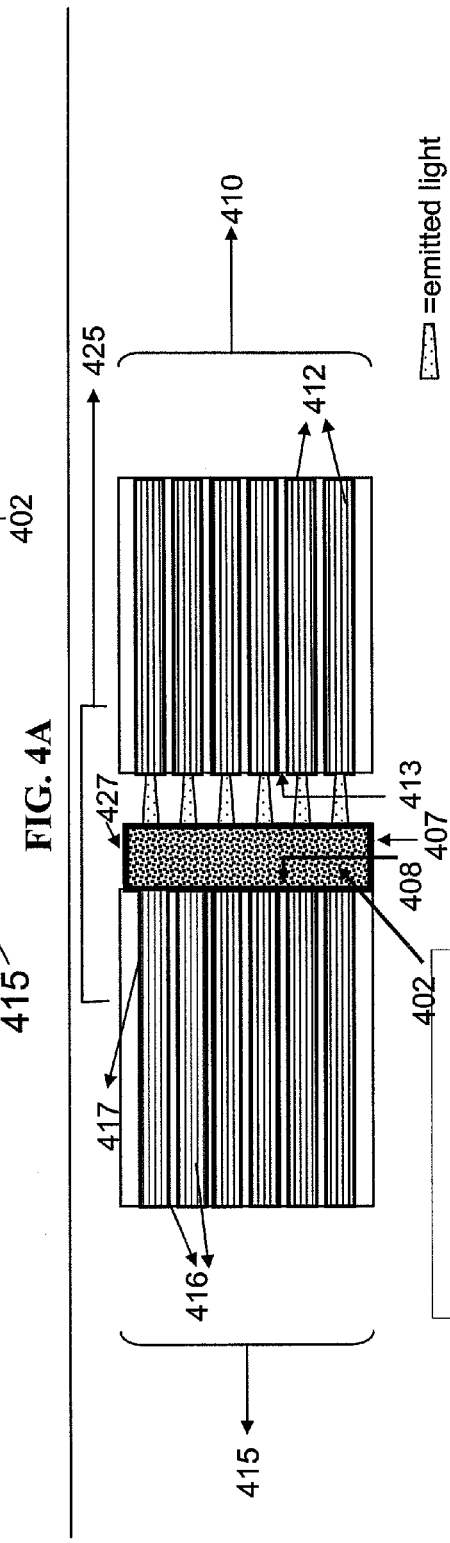
FIG. 4B provides a schematic drawing illustrating fiber optic bundles and light emission in an illustrative glucose sensor of the present invention that includes a closer view of the coupling region 425 where the detection bundle 415 receives light from the emitter bundle 410.
Figure 4C:
FIG. 4C provides a schematic drawing of a cross-sectional view of a detection bundle (also called a receiver bundle) 415 and an emitter bundle 410.

In certain illustrative examples, such as the glucose sensor illustrated in FIG. 3, FIG. 4, and Example 2, an array of fiber optic fibers are used as the emitters 410 to emit light toward a ½ circular bundle of fiber optic fibers, the receivers 415. The array of emitter fiber optic fibers 410 can be formed into a loop such that light emitting from the end of the emitter fiber optic fibers 410 travels in a second direction 478 that is substantially opposite, or opposite, to light that enters the emitter fiber optic fibers in a first direction 475 produced by a light source 490. Therefore, in these aspects the emitters and the receivers can enter the glucose sensor 400 through a first end 482 of the glucose sensor 400. This design makes it much more convenient for connecting the glucose sensor to a light source 490, photodetector 495, and/or signal processing unit 498. Furthermore, this design improves the signal to noise ratio of the device over one relying on measurements of scatter, reflection, absorption or other optical phenomena in which light is emitted and detected from/by the same bundle. Since emitter fiber optic fibers are easily aligned with receiver fiber optic fibers the amount of light collected can be orders of magnitude greater. The emitter fiber optic bundle and the receiver fiber optic bundle can be a circular bundle, ½ circular bundle, or a side-by-side array, but in illustrative examples the emitter bundle is a side-by-side array and the receiver bundle is a circular or ½ circle fiber bundle.

In another embodiment, provided herein is a spectrometer comprising a light source, a photodetector, an emitter fiber optic fiber or an emitter fiber optic bundle of fibers, for emitting light from the light source to a detection region, and a receiver fiber optic fiber, or a receiver fiber optic bundle of fibers, for receiving light emitted by the emitter fiber optic fiber and transmitting the light to the photodetector, wherein the emitter fiber optic fiber forms a loop such that light emitting from the emitter fiber optic fiber travels in a second direction that is substantially opposite, or opposite, to light produced by a light source that enters the emitter fiber optic fibers in a first direction. As will be understood, many of the teachings provided herein directed to the sensing region of a biosensor apply to the detection region of the spectrometer of the present invention. In fact, it will be understood that a sensor according to the present invention utilizes a spectrometer of the present invention for its detection and analyte measuring functions. For example, in certain aspects of the spectrometer, as well as in aspects of a biosensor of the present invention, such as a glucose sensor, the emitter fiber optic fiber and the receiver fiber optic fiber can enter the microspectrometer through a first end. In a related embodiment, provided herein is a method for optically analyzing a sample by transmitting light from a light source into an emitter fiber optic fiber through a sample into a receiver fiber optic fiber in optical communication with the emitter fiber optic fiber, wherein light travels from the light source through a loop in the emitter fiber optic fiber, or bundle of fiber optic fibers, such that light exiting from the emitter fiber optic fibers travels in a second direction that is substantially opposite, or opposite, to light produced by a light source that enters the emitter fiber optic fibers in a first direction. Therefore, in these aspects light can enter and exit the spectrometer from a first end, which combined with the small size of the device, simplifies and improves the possible uses for a spectrometer provided herein.

Virtually any light source and photodetector can be used for the spectrometer or sensor of the present invention, such as a glucose sensor. The light source can be broad or narrow banded in the light spectrum and can be from a selection of multiple bands available to the emitter fiber optic fiber(s). In certain aspects, the light source is a laser light source, an LED, an incandescent light bulb, an arc lamp, and in illustrative embodiments the light source is a laser diode. The emitter fiber optics fibers can be connected internal or external optics or optoelectronics to control the wavelength, intensity, polarization, pulse width, or other optical characteristics of the light. The receiver fiber can be connected to additional internal or external optics or optoelectronics for measuring intensity, polarization, fluorescent decay or other optical properties in narrow or wide bands of the light spectrum. It will be understood that although the invention is illustrated herein by the use of a light source and a photodetector, other types of energy sources and detectors, respectively, can be used.

In an alternative sensing scheme, an oxygen sensitive dye can be placed at the sensing boundary 008 of a biosensor or spectrometer provided herein. The dye can then be probed optically to monitor the oxygen field and assess the glucose concentration.

The detector 495, light source 490, and signal processing unit 498 are connected to one end of the biosensor or spectrometer provided herein. In certain illustrative examples, the detector 495, light source 490, and signal processing unit 498 are housed within the same assembly. For glucose sensors provided herein, typically probes of the sensors, or thin tubes or wires or other coverings that house the probes, pass through the skin and connect to a housing outside the skin that includes the detector 495, light source 490, signal processing unit 498 and in the case of internalized electronics, supporting electronics. Accordingly, in these illustrative examples, the device is a transdermal device. In certain aspects of a transdermal device a non-disposable unit external to the skin is connectorized to connect with a disposable implantable needle-type sensor connectorized on its back end. In such a scenario, the two units are connected together such that, in one illustrative example, light sources and photodetectors within the nondisposable unit are aligned, via the connection, with light guides housed in the disposable needle-type sensor which terminate appropriately near or adjacent to the glucose reaction zone within the disposable implant. The nondisposable unit manages timing of measurements, data analysis, power supply, communication with the patient, etc. . . . which the disposable unit houses the sensor probe.

In certain illustrative aspects, as illustrated in Example 2, spatial sampling of the reaction region is achieved by turning on certain emitter fibers at different times. For example, individual emitter fibers 412, adjacent pairs of emitter fibers, or adjacent trios of fibers within an emitter array 410 can be turned on and off in order from closest or furthest from the glucose inlet 7, to the opposite end. In these aspects, a single photodetector 495 can be used to measure light at each time point that a pair of emitter arrays 410 is turned on. These measurements can be used to recreate the spatial oxygen and glucose content of the reaction region 002, and provide a substantial increase in signal to noise ratio over aspects where all emitter fibers are turned on simultaneously.

In certain aspects, because the reduction of glucose results in peroxide, the surrounding tissues can be protected from any such secretions from the sensor. This can be accomplished by reducing the peroxide to water and oxygen in the space immediately surrounding the reaction chamber via the enzymatic reaction of peroxide with catalase.

To prevent the drift in the oxygen sensing process, agents (e.g. catalase, dehydrogenases) can be added to prevent any free radicals that are created during the optical interrogation from degrading the hemoglobin emulsion. One such agent is blood serum albumin, which can also be used as soluble carrier proteins for crosslinking to the glucose oxidase. The glucose oxidase enzyme is crosslinked to the bovine serum albumin to stabilize enzyme activity over the period of monitoring. In certain aspects the soluble carrier protein may be bovine serum albumin, human serum albumin, and/or gelatin. At high glucose oxidase concentrations (on the order of 70% or greater) it may be unnecessary to add the soluble carrier proteins to form a hydrogel (See e.g., Clark, U.S. Pat. No. 6,815,186). As a general method according to the present invention, initial albumin concentrations from 15 g/L to 25 g/L can be used in formation of the matrix or hydrogel. This value is based on the range of normal human albumen which is 35-47 g/L, divided by two (assuming a hematocrit of 50%) (data from the worldwide web at hoslink.com/LabResults/refranges.htm).

Glucose sensors provided herein can be calibrated before implantation by exposing them to bulk oxygen concentrations from 3% to 7% and from glucose concentrations from 30 mg/dl to 500 mg/dl. The individual profiles monitored are then used to precisely quantitate unknown glucose measurements in the presence of variable bulk oxygen tensions.

The following examples are intended to illustrate but not limit the invention.

EXAMPLE 1

Analysis of the Oxygen Conducting Capability of Hemogloblin

The following example illustrates the oxygen conducting capability of hemoglobin and the intended functionality of the reversible oxygen binding protein. A film of hemoglobin was prepared as follows. Human blood was extracted with a finger-stick device. A large drop of the blood was deposited on one end of a rectangular microscope glass slide. A blood smear ⅛ inches by 1½ inches in dimension was created by sliding a microscope cover glass from the blood drop, across the glass slide to create a thin film of blood across the glass slide. The glass slide was then covered in cellophane leaving approximately ¼ inch of the blood smear exposed in the long axis. A glass coverslip was placed on the cellophane to ensure a good seal. This setup ensures no-flux oxygen boundaries on all surfaces and edges of the blood smear, except for at the exposed ¼ inch at the end. A diode laser's beam was directed through the glass slide, blood smear, cellophane, and cover glass at a point 1 inch from the exposed boundary. Light leaving the sample was measured by a photodiode. The photodiode voltage, which is proportional to light collected was monitored over time before, during and following changing oxygen concentrations at the exposed boundary.

Figure 2:
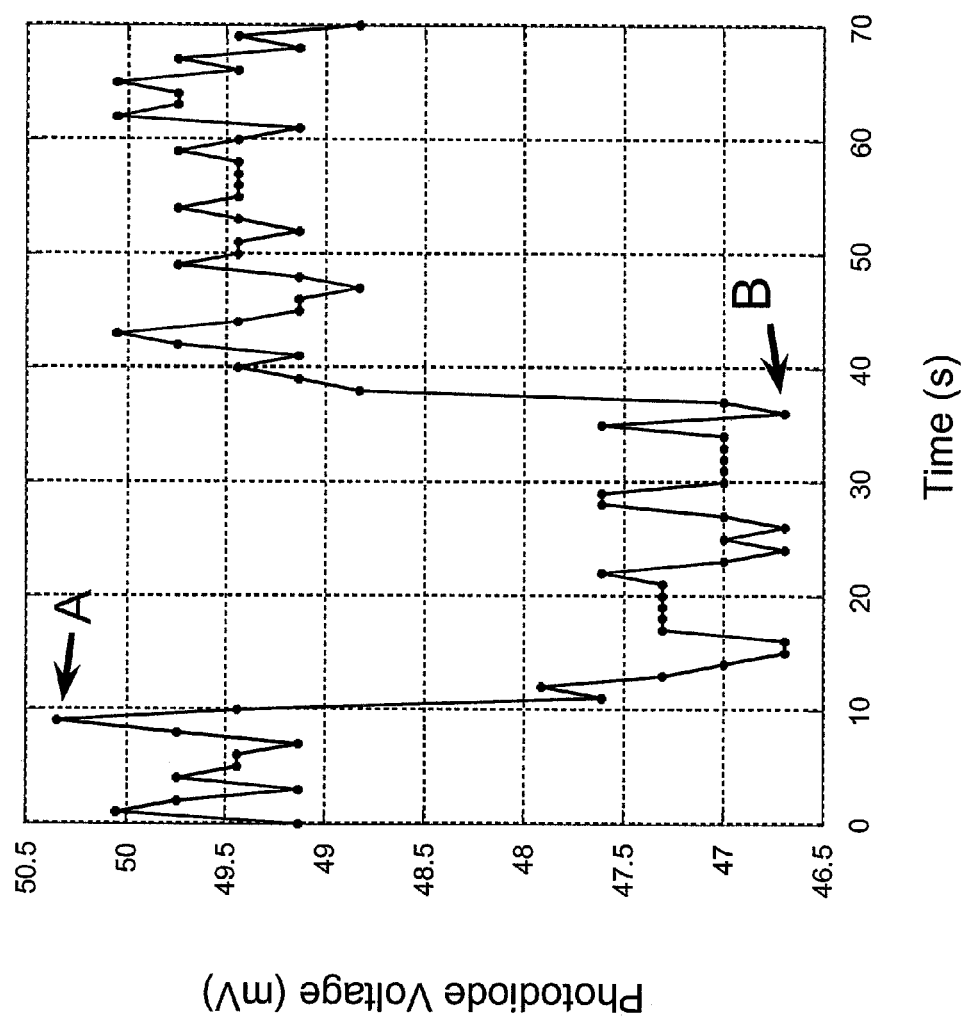
FIG. 2 is a plot of photodiode voltage corresponding to diode laser transmission through a Hemoglobin (Hb) film bound in an oxygen impermeable membrane save for a small region at one end exposed to its surroundings. The signal represents the changing Hb absorption at 635 nm laser light. In the time preceding reference 'A' room air was applied at the exposed region of the Hb film. At reference 'A', a 5% oxygen gas mixture was applied to the exposed region of the Hb film, followed by room air again applied to the exposed region of the Hb film at reference 'B'.

The signal in FIG. 2 represents the changing Hemoglobin absorption at 635 nm laser light. This figure shows the photodiode response first for the transition from room air at the boundary to a 5% oxygen, 95% nitrogen gas mixture (arrow A), and then for the transition from that gas mixture back to room air (arrow B). As can be seen, the photodiode voltage changes only seconds after the boundary condition changes. Therefore a significant amount of oxygen moved 1 inch within seconds, a rate far beyond that expected by diffusion. This experiment is fundamentally identical to the oxygen transport scenario within the sensor implanted in the body; the oxygen transport region will be proximal to the high oxygen tension arterioles and capillaries and will be coupled to the reaction zone where oxygen will be consumed. This experiment demonstrates that the oxygen from the body can be rapidly directed to the site of the enzymatic reaction where it is needed.

EXAMPLE 2

Illustrative Implantable Glucose Sensor

This Example discloses certain features of an illustrative glucose sensor 400 of the present invention, as illustrated in FIG. 3 and FIG. 4, and exemplifies a method for manufacturing the illustrative glucose sensor 400. In the illustrative glucose sensor 400 provided in this example and illustrated in FIG. 3, the electronic light source 490 and the photodetector 495 communicate through a series of fiber optic bundles 410, 415 with the illustrative glucose sensor 400. In the method used to create the glucose sensor 400, an array of individual optical fiber emitters 410 was bent into a hook so that light emanating from the emitter array 410 traveled through the reaction zone 402 and was collected by a detection fiber optic bundle 415 (i.e. an array of optical fiber receivers). In this illustrative glucose sensor 400 the entire back end of the detection bundle 415 was coupled to a photodiode type photodetector 495.

During use of the glucose sensor 400, spatial sampling of the reaction zone 402 was accomplished by changing the pattern of emission down the emission array 410. In one exemplary method, adjacent pairs of emitter fibers within the array 410 were turned on in order from closest to the glucose entry boundary (i.e. glucose inlet) 407 inwards towards the oxygen reference region where the oxygen reference region is at least as far from the glucose inlet as the distance, in a direction pointing along the surface normal of the glucose inlet, at which oxygen concentration changes are glucose independent, each time recording the output of the single photodiode. The oxygen reference region was the region within the glucose reaction region 402, running between 200 um from the glucose inlet to the border 427 of the glucose reaction region opposite the glucose inlet 407. This border region 427 opposite the glucose reaction region in the illustrative glucose sensor was approximately 300 um from the glucose inlet 407. By knowing the emission source corresponding to each output result, the spatial content of the reaction zone can be reconstructed. A key advantage to this mode of operation over that in which all emission fibers are on simultaneously and the detection bundle is broken into subsets, each with its own photodetector 495, is the substantial increase of the signal over the noise. Details of the method that was used to make the illustrative glucose sensor 400 are provided in the following paragraphs.

The Implant Needle 480

Implant needles 480 were custom build by modifying commercially available 23 gauge syringe needles. A window 470 was carved at a point on the side or wall of the needle between the tip 481 of the needle 480 and the back end 482 of the needle 480 using a high speed rotary tool with a ceramic tip. The window 470 was cut 1 mm long, and spanned about ½ the curvature or circumference of the needle 480. The tip of the rotary tool was chosen to smooth the boundary of the window between the outer and inner wall of the needle while the rotary tool cuts. The goal of the smoothing was to minimize surface tension boundaries, and to facilitate the entry of tissue into the space between the inner and outer walls of the window's boundary to minimize diffusional distances to the reaction zone The Emission Array 410

The emission array 410 was a linear array of individual fibers 412 with a cladding diameter (i.e., an outer diameter) of either 40 μm or 50 μm and a numerical aperture of 0.54, 0.57, or 0.64. The fibers 412 had a numerical aperture of 0.54. The total length of the array 410 was slightly smaller than the inner diameter of the implant needle 480. For this illustrative example, that corresponded to approximately 10 fibers. It was found that when coupling emission fibers 412 to the primary laser output fiber coupler using a multimode FC connector with a 125 μm bore, pairs of fibers couple as efficiently as triplets. Additionally single fibers 412 coupled poorly, likely as a result of bending about the optical axis due to stresses in the fiber 412, and the extra room in the connector. Triplets of fibers do not fit linearly within the coupler, and sample a larger volume of the reaction zone. As such, we chose to couple pairs of individual fibers 412 within the emission array 410, each to their own laser source.

A notable feature of this illustrative glucose sensor 400 is the 180 degree bend in the emitter array 410 allowing the emitter array 410 to enter the back 482 of the implant needle 480, to pass the reaction window 470 carved in the needle 480, and then to turn around in the needle 480 and align in a parallel orientation adjacent to the detection bundle, also referred to herein as the receiver bundle 415, as illustrated in FIG. 3. Thus, the emission bundle 410 and the detection bundle 415, run parallel for a stretch of the illustrative glucose sensor 400 at the back end 482 where the emission bundle 410 and the detector bundle 415 enter the glucose sensor 400. The bend 414 in a single fiber 412 is formed by inserting it into a 30 gauge needle to form a loop and reducing the size of the loop until just slightly larger than its breaking point. A heating source, in this case a cigarette lighter flame was applied momentarily to melt the fiber and cause it to yield to the applied stresses induced by the bending. Likewise a set of fibers can be bent as a group by feeding them in to a 28 gauge needle and forming a loop slightly larger than the size at which they break. Again, a cigarette lighter flame was applied briefly to the fibers to cause them to yield to the stresses applied by the loop. In both cases, if the resulting loop is too large in its bending radius, the process may be repeated by further retracting the loop into the needle to place additional stress on the formed loop and momentarily heating the loop with the flame from a cigarette lighter, actually a Quicker Clicker™ lighter for a fireplace log. After testing the flame from a variety of sources, including a butane pencil torch, a match, a propane torch, and a map torch, it was found that only a very small flame was needed, and that too large of a flame caused unintended bending out of the intended plane of the loop. The area of the emission array is small enough compared to the overall area of the glucose sensor and the overall volume within the lumen of the needle such that an oxygen transport region 401 can surround the emission array in the lumen of the needle 480 beyond the reaction window 470 and still function as originally intended.

The Detection Bundle 415 (Also Referred to Herein as a Receiver Bundle)

The detection bundle 415 in the illustrative example is a circular bundle of individual fibers 416, in which one half of the circular cross-section is removed. That is, in cross-section the bundle forms ½ a circle. The geometry facilitates hand manufacturing at a high throughput rate. For large volume fabrication, alternate geometries can be used. Bundles were constructed two at a time by constructing a circular bundle, and then splitting the bundle into two semicircular cross-sectional bundles, each used in its own device. The circular bundles were constructed by filling a smaller gauge needle (28 gauge) with as many individual fibers as possible. 50 μm fibers as described above in the emission array 410 section were used. The individual fibers 416 are then held together using nail polish according to the following protocol. The individual fibers 416 are threaded into the needle from the pointed end 481 of the needle 480, and out the blunt back end 482 by at least one inch. A generous amount of nail polish is deposited at the back end 482 of the needle 480, held in place by the surface tension of the needle/fiber/polish interface. The bundle 415 is then drawn back into the needle, past the blunt end 482, and then advanced again so the end of the bundle 415 aligns with the blunt end of the needle. At a time before curing of the nail polish is complete, the bundle 415 is again advanced out of the needle 480, allowing the fibers 416 to cure but not be adhered to the needle 480. Before curing is complete, the bundle 415 is carefully split in half with a sharp Exacto™ knife blade, along a diameter of the cross-section and allowed to cure. The end result is two half-circular cross-sectional bundles.

Depositing the Reaction Region 402 onto the Detection Bundle 415

In this illustrative glucose sensor, the reaction region (also called the reaction zone) 402 is deposited onto the detection bundle surface 408 outlined below.

1. The detection bundle pair was either reinserted into the pointed end of a 28 gauge needle or remained in the 28 gauge needle used to form the bundle pair, and aligned with the blunt back end 482.

2. The end of the detection bundle 415 and the emitter bundle 410 was polished to increase light collection efficiency. We have found that an increase in light collection efficiency of approximately 3× can be achieved by polishing the collecting end of the detection bundle 415 and the emitting end of the emitter bundle 410. Polishing was achieved first by slightly advancing the bundle beyond the blunt end 482 of the 28 gauge needle and then by gliding the bundle end on a series of polishing papers of increasing fineness as using known techniques to polish fibers by hand. "Thor's Guide to Connectorization and Polishing Optical Fibers" Thor Labs, Newton, N.J., 1997.

3. Fiber bundle tip was dipped in solution of 0.1% (w/v), or equivalently 1 μg/ml, poly-lysine in deionized water. The poly-1-lysine was used to facilitate the adhesion of biomolecules to the end of the detection bundle 415. Polished glass has poor adhesion to biomolecules.

4. The prepared Reaction region mixture is deposited onto tip of bundle 408. The reaction mixture is a stabilized matrix comprised of hemoglobin, an engineered hemeprotein or a heme derivative such as myoglobin, the enzyme glucose oxidase, a carrier protein such as albumin, and a fixative such as glutaraldehyde This is accomplished by first drawing the bundle 415 back into the 28 gauge needle approximately 2 mm from the blunt end of the needle. The blunt end of the needle is used to cut the reaction zone matrix, which has been deposited onto a flat surface such a glass slide, into the exact shape of the needle's inner lumen, analogous to a cookie cutter. Two variations were used to accomplish this step
  a. An entire circular bundle 415 was used, and split into two bundles after depositing the reaction zone
  b. A pair of half-circle bundles 415 were used 5 The bundle 415 is carefully pushed back though the blunt end of the 28 gauge needle, carrying the cut reaction zone 402 with it.

6. The needle is removed from the bundle 415, and the bundle 415 is dipped into a silicon adhesive diluted with Toluene at a ratio of 6:1 Toluene to adhesive, to coat the bundle tip and reaction zone 402 with an oxygen permeable, glucose impermeable membrane.

Assembly of the Illustrative Glucose Sensor 400

The illustrative glucose sensor 400 was assembled by aligning the emission array 410 with the detection array 415 outside of the implant needle 480 such that the reaction region 402 is between the emission array 410 and the detection array 415, and then sliding the aligned emission array 410, reaction region 402, and detection array 415 (i.e. the coupled light system) back into the needle 480 such that the coupling region (i.e. the region between the emission array 410 and the detection array 415, which includes the glucose reaction zone and in which light from the emission array 410 is received by the detection bundle 415) is within the reaction window 470 cut into the needle 480. The steps are outlined below in more detail.

1. The detection bundle 415 and the emitter bundle 410 are both either advanced up through the implant needle 480, or backed down through the needle 480 so that a few inches of both extend beyond the pointed end 481 of the needle 480, including the bend 414, and emitting end 413 of the emitter bundle 410 and the receiving end 408 of the detection bundle 415, and length of the detection bundle 415 and the emitter bundle 410 extends well beyond the back end of the implant needle.

2. The emitting end 413 of the emission bundle 410 is positioned near the receiving end 408 of the detection bundle 415 until maximum transmission is achieved through the back end of the detection bundle 415. This position will correspond to a geometry in which the linear array of the emission bundle 410 is aligned transversely to the linear boundary of the half-circular bundle. That same boundary, along with the linear shape of the emission bundle 410 remove rotational degrees of freedom from the alignment procedure. Ideally, the system is constructed so only the axial placement is critical, but some transverse translation of the emitter bundle 410 relative to the detector bundle 415 may be required.

3. An adhesive such as silicon or nail polish is applied along the longitudinal coupling of the emission bundle 410 and detection bundle 415 behind the optical coupled region. This step stably locks the two fiber systems together.

4. The coupled light system is then backed into the needle 480 so that the coupling is within the reaction window 470 cut into the needle 480.

5. The length of the needle 480 between the reaction window 470 and the tip 481 of the needle is filled with the oxygen transport region 401 material and allowed to dry. The oxygen transport region is a stabilized matrix comprised of hemoglobin, an engineered hemeprotein or a heme derivative such as myoglobin, a carrier protein such as albumin and a fixative such as glutaraldehyde. The mixture is applied to the sensor before its cure time has completed such that it still behaves as a liquid.

6. A glucose entry pinhole 407 is cut into the side of the reaction zone 402 using a the pointed tip of a small syringe needle to allow glucose to enter into the reaction zone.

7. The reaction window 470 is covered with a glucose and oxygen permeable membrane.

The entire needle 480, or only the reaction window region 470 is covered with a biocompatible membrane. For example, the membrane can be a membrane with approximately 5 μm pores to promote immune reaction resistance.

EXAMPLE 3

Glucose Measurements Using an Illustrative Sensor

This Example demonstrates detection of glucose in a relatively simple glucose sensor that includes two stabilized oxygen transport matrices in communication with one another. One of the illustrative stabilized oxygen transport matrices was an oxygen transport region and the other was a glucose reaction region that included a stabilized glucose oxidase-hemoglobin thin gel.

A contiguous oxygen transport region and glucose reaction region were deposited on a glass slide, coated with silicon, and a glucose inlet was present on a surface of the glucose reaction region. The glucose reaction region was made with 20 mg glucose oxidase and 0.1 ml of human blood crosslinked with a dilute formaldehyde solution. The steps for constructing the glucose reaction region are outlined below in more detail.

1. 0.1 ml of whole human blood was combined with 0.3 ml of a solution containing a 1:3 ratio of 70% isopropyl alcohol to distilled water to lyse the red blood cell membranes.

2. 20 mg glucose oxidase was added to the lysed blood cell mixture of step 1. The mixture contained no visible glucose oxidase precipitate following adequate mixing.

3. Using the edge of a glass coverslip, a portion of the mixture of step 2 was transferred to the bottom portion a glass slide to form a thin strip across short dimension of the slide. The width of the strip was 2 mm.

4. The mixture was allowed to dry on the glass slide.

6. The glass slide was immersed in a 4% formaldehyde solution for 10 minutes and then rinsed with 70% isopropyl alcohol and allowed to dry The oxygen transport region was made with 0.1 ml of human blood crosslinked with a dilute formaldehyde solution. The steps for constructing the oxygen transport reaction region and completing the sensor are outlined below in more detail.

1. 0.1 ml whole human blood was combined at a 1:3 ratio to a solution containing a 1:3 ratio of 70% isopropyl alcohol to distilled water to lyse the red blood cell membranes 2. The mixture was mixed to a uniform consistency and about ½ of it was applied to the glass slide containing the glucose reaction region so that the mixture covered the majority of the glass slide across its short dimension and formed a contiguous layer with the glucose reaction region. The mixture was allowed to dry.

3. The entire preparation on the glass slide was covered with a thin layer of silicon rubber. Using a very sharp blade, parallel grooves were cut through the silicon rubber and the deposited layers. A sensor is thus defined by the contiguous regions between two parallel grooves. The silicon was blow dried with cool air to accelerate curing.

4. Using the tip of a syringe needle, a glucose inlet was cut through the silicon at the intersection of one of the grooves and the glucose reaction region just below where the oxygen transport region and the glucose reaction region connect.

Figure 6:
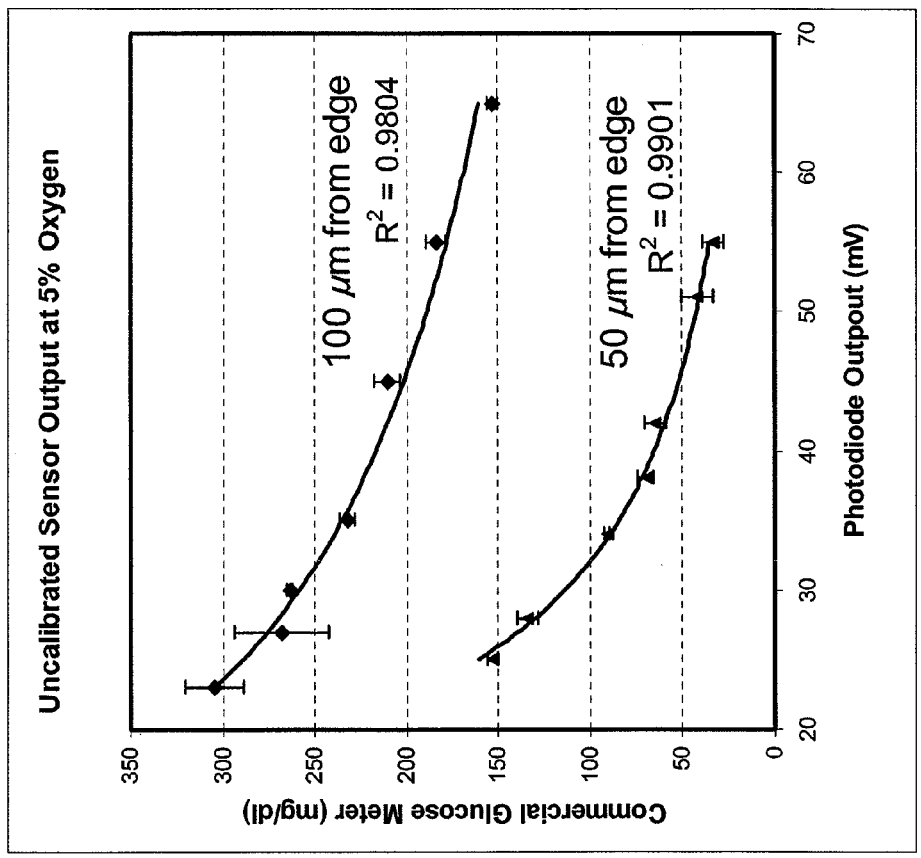
FIG. 6 illustrates detection of glucose in a stabilized glucose oxidase-hemoglobin thin matrix The results are presented as plots of glucose concentrations within a water bath with a 5% $O_2$+95% $N_2$ gas mixture bubble in, plotted against the corresponding photodiode voltage when the reaction gel was interrogated at a location of 50 um or 100 um from the glucose inlet 7.

The glass slide was suspended in a water bath with a [5% $O_2$+95% $N_2$] gas mixture bubbled in. The reaction zone was optically probed by focused laser light in a spot approximately 10 um in diameter positioned 50 um or 100 um from the glucose inlet along the axis of the injector surface. Laser light was recollected onto a photodiode whose electrical current was converted to voltage and recorded across a clinical range of glucose solutions in the bath. FIG. 6 shows graphs of glucose concentrations within the bath plotted against the corresponding photodiode voltage when the reaction gel was interrogated at a location of 50 um or 100 um from the entrance for glucose (i.e. the glucose inlet). The graphs demonstrate the utility of spatial sampling within the reaction zone. The interrogation spot 50 um in from the glucose inlet demonstrated good sensitivity to glucose concentration changes at lower glucose concentrations, but looses sensitivity near 150 mg/dl at which point the power function relationship transitioned into steepness. The interrogation spot located 100 um in from the glucose inlet demonstrated good sensitivity at 150 mg/dl up to at least 300 mg/dl. Information from the two locations together yields good sensitivity across the clinical range of glucose concentrations. Glucose solutions were measured in triplicate using a TrueTrack™ over-the-counter glucose meter co-branded by Say-On/Osco/Albertsons and Home Diagnostics, Inc.

Figure 7:
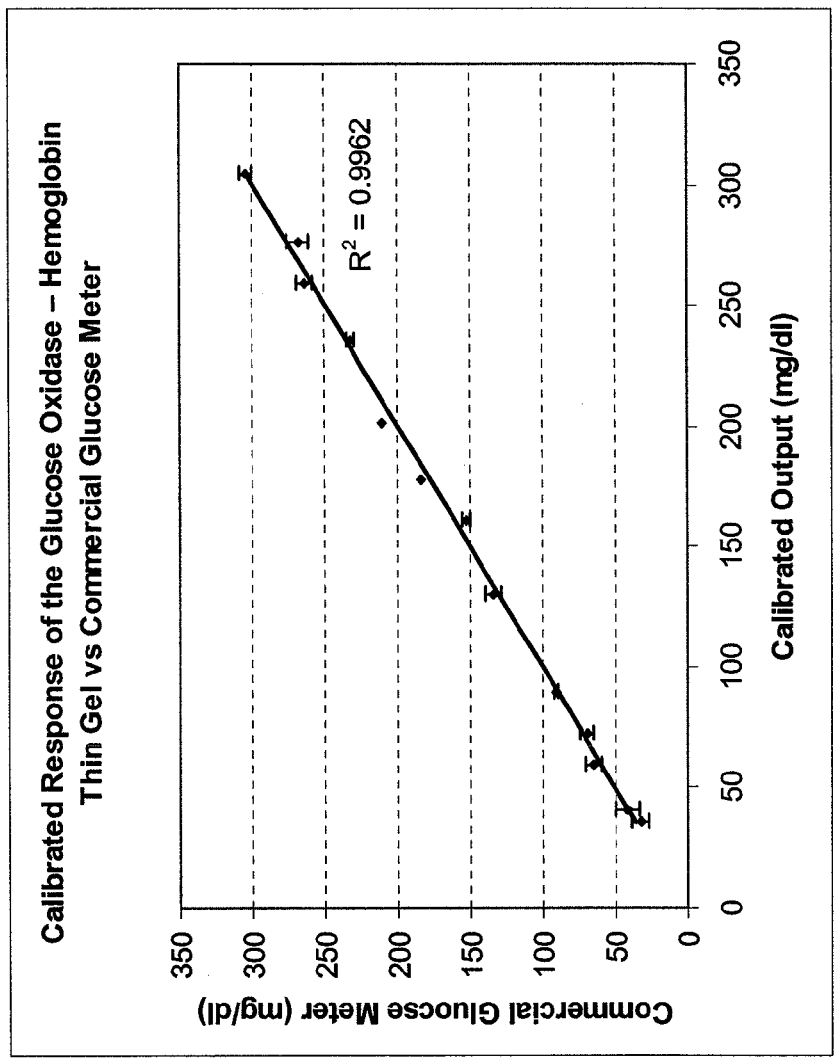
FIG. 7 shows the calibrated response of the glucose oxidase-hemoglobin thin gel of FIG. 6 plotted against the TrueTrack™ glucose meter measuring the same glucose solutions.

FIG. 7 shows the calibrated response of the glucose oxidase-hemoglobin thin gel of FIG. 6 plotted against the TrueTrack™ glucose meter measuring the same glucose solutions. A linear fit yields an $R^2$ value of 0.99, thus demonstrating that results obtained using the illustrative.

Although the invention has been described with reference to the above example, it will be understood that modifications and variations are encompassed within the spirit and scope of the invention. Accordingly, the invention is limited only by the following claims.

What is claimed is:

1. A sensor for measuring an analyte, the sensor comprising:
    an oxygen transport region comprising at least one reversible oxygen binding protein;
    an analyte reaction region, the analyte reaction region comprising:
        an oxygen-permeable surface in communication with the oxygen transport region;
        an analyte-permeable surface configured to allow a target analyte to pass through, the analyte-permeable surface located generally orthogonal to the oxygen-permeable surface; and
        an analyte reaction chamber at least partially surrounded by the oxygen-permeable surface and the analyte-permeable surface, the reaction chamber configured to retain a target analyte oxidase enzyme;
        wherein the oxygen-permeable surface, the analyte-permeable surface, and the analyte reaction chamber are configured to form an oxygen gradient in the analyte reaction region; and
    a sensing region comprising at least one detector, wherein the detector is configured to spatially sample the oxygen gradient within the analyte reaction region.

2. The sensor of claim 1, wherein the analyte-permeable surface is smaller than the oxygen-permeable surface.

3. The sensor of claim 1, wherein the sensor is substantially non-oxygen consuming.

4. The sensor of claim 1, wherein the oxygen transport region comprises a hemeprotein, or an engineered heme derivative.

5. The sensor of claim 1, wherein the target analyte is selected from the group consisting of glucose, galactose, lactose, peroxide, cholesterol, amino acids, alcohol, lactic acid and mixtures thereof.

6. The sensor of claim 1, wherein the analyte passes through the analyte-permeable surface from a first portion to a second portion and the oxygen gradient has more oxygen near the second portion than the first portion.

7. The sensor of claim 1, wherein the oxygen gradient is dependent on analyte and target analyte oxidase levels.

8. The sensor of claim 1, wherein the analyte reaction region further comprises a reference region, wherein analyte concentration in the reference region is sufficiently low so as not to measurably reduce oxygen concentration in the reference region.

9. The sensor of claim 8, wherein the analyte passes through the analyte-permeable surface from a first portion to a second portion and the reference region is located after the second portion, so that the second portion is located between the first portion and the reference region.

10. The sensor of claim 9, wherein a size of the reference region depends on a reaction rate of glucose near the first portion.

11. The sensor of claim 8, wherein the reference region provides an analyte insensitive oxygen reference concentration.

12. The sensor of claim 8, wherein the at least one detector is configured to measure oxygen concentration in the reference region.

13. The sensor of claim 1, wherein the sensor is configured to be a transcutaneous sensor.

14. The sensor of claim 1, wherein the analyte is glucose.

15. The sensor of claim 1, wherein the sensor is implanted in subcutaneous tissue.

* * * * *